United States Patent
Gonzalez et al.

(10) Patent No.: US 11,697,830 B2
(45) Date of Patent: Jul. 11, 2023

(54) ITERATIVE PLATFORM FOR THE SYNTHESIS OF ALPHA FUNCTIONALIZED PRODUCTS

(71) Applicants: Ramon Gonzalez, Tampa, FL (US); James M. Clomburg, Houston, TX (US); Seokjung Cheong, Emeryville, CA (US)

(72) Inventors: Ramon Gonzalez, Tampa, FL (US); James M. Clomburg, Houston, TX (US); Seokjung Cheong, Emeryville, CA (US)

(73) Assignee: Ramon Gonzalez, Tampa, FL (US)

( * ) Notice: Subject to any disclaimer, the term of this patent is extended or adjusted under 35 U.S.C. 154(b) by 0 days.

(21) Appl. No.: 16/818,642

(22) Filed: Mar. 13, 2020

(65) Prior Publication Data
US 2020/0325502 A1    Oct. 15, 2020

Related U.S. Application Data

(63) Continuation-in-part of application No. 15/566,704, filed as application No. PCT/US2016/027873 on Apr. 15, 2016, now abandoned.

(60) Provisional application No. 62/148,123, filed on Apr. 15, 2015.

(51) Int. Cl.
| | |
|---|---|
| *C12N 9/02* | (2006.01) |
| *C12P 7/42* | (2006.01) |
| *C12N 9/00* | (2006.01) |
| *C12N 9/10* | (2006.01) |
| *C12N 9/04* | (2006.01) |
| *C12N 9/16* | (2006.01) |
| *C12N 9/88* | (2006.01) |

(52) U.S. Cl.
CPC ................ *C12P 7/42* (2013.01); *C12N 9/001* (2013.01); *C12N 9/0006* (2013.01); *C12N 9/0008* (2013.01); *C12N 9/1029* (2013.01); *C12N 9/13* (2013.01); *C12N 9/16* (2013.01); *C12N 9/88* (2013.01); *C12N 9/93* (2013.01); *C12Y 101/01036* (2013.01); *C12Y 102/0101* (2013.01); *C12Y 103/01044* (2013.01); *C12Y 402/01119* (2013.01)

(58) Field of Classification Search
None
See application file for complete search history.

(56) References Cited

U.S. PATENT DOCUMENTS 8,163,980 B2 *  4/2012  Ro ..................... C12N 9/0042
                                                        800/287

FOREIGN PATENT DOCUMENTS

WO    WO-2012109176 A2 *  8/2012  ................ C12P 7/16

OTHER PUBLICATIONS

Prather et al., Current Opinion in Biotechnology, vol. 19, pp. 468-474, 2008.*
Kizer et al. (Applied and Environmental Microbiology, vol. 74, pp. 3229-3241, 2008.*
Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard G Hutson
(74) *Attorney, Agent, or Firm* — Boulware & Valoir

(57) ABSTRACT

The use of microorganisms to make alpha-functionalized chemicals and fuels, (e.g. alpha-functionalized carboxylic acids, alcohols, hydrocarbons, amines, and their beta-, and omega-functionalized derivatives), by utilizing an iterative carbon chain elongation pathway that uses functionalized extender units. The core enzymes in the pathway include thiolase, dehydrogenase, dehydratase and reductase. Native or engineered thiolases catalyze the condensation of either unsubstituted or functionalized acyl-CoA primers with an alpha-functionalized acetyl-CoA as the extender unit to generate alpha-functionalized β-keto acyl-CoA. Dehydrogenase converts alpha-functionalized β-keto acyl-CoA to alpha-functionalized β-hydroxy acyl-CoA. Dehydratase converts alpha-functionalized β-hydroxy acyl-CoA to alpha-functionalized enoyl-CoA. Reductase converts alpha-functionalized enoyl-CoA to alpha-functionalized acyl-CoA. The platform can be operated in an iterative manner (i.e. multiple turns) by using the resulting alpha-functionalized acyl-CoA as primer and the aforementioned alpha-functionalized extender unit in subsequent turns of the cycle. Termination pathways acting on any of the four alpha-functionalized CoA thioester intermediates terminate the platform and generate various alpha-functionalized carboxylic acids, alcohols and amines with different β-reduction degree.

3 Claims, 30 Drawing Sheets

Specification includes a Sequence Listing.

Lane 1: Ladder;
Lane 2: Cell extract fraction of *S. cerevisiae* pYES260-HACL1-ScOpt;
Lane 3: HACL1 purified from *S. cerevisiae* pYES260-HACL1-ScOpt

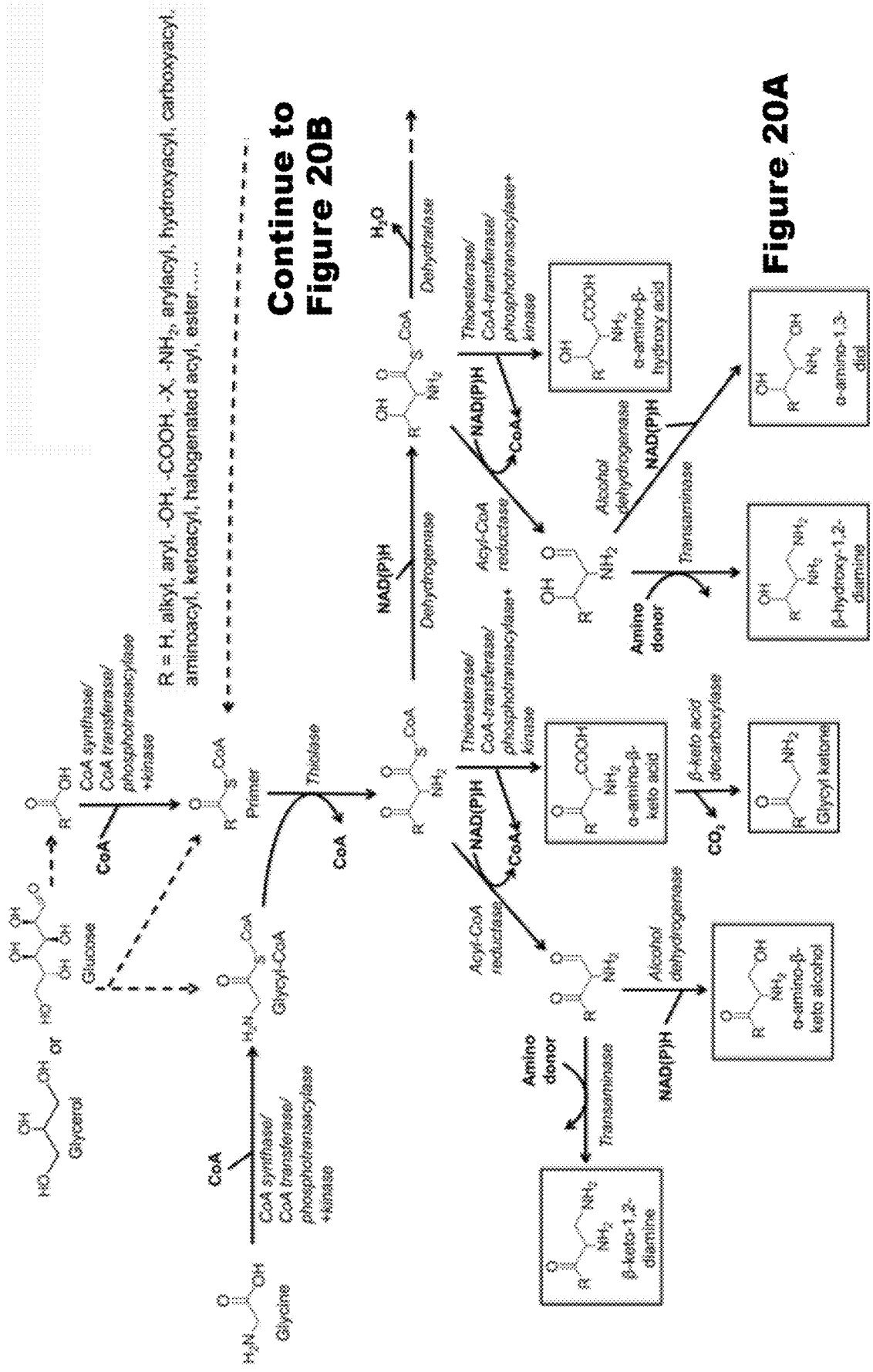

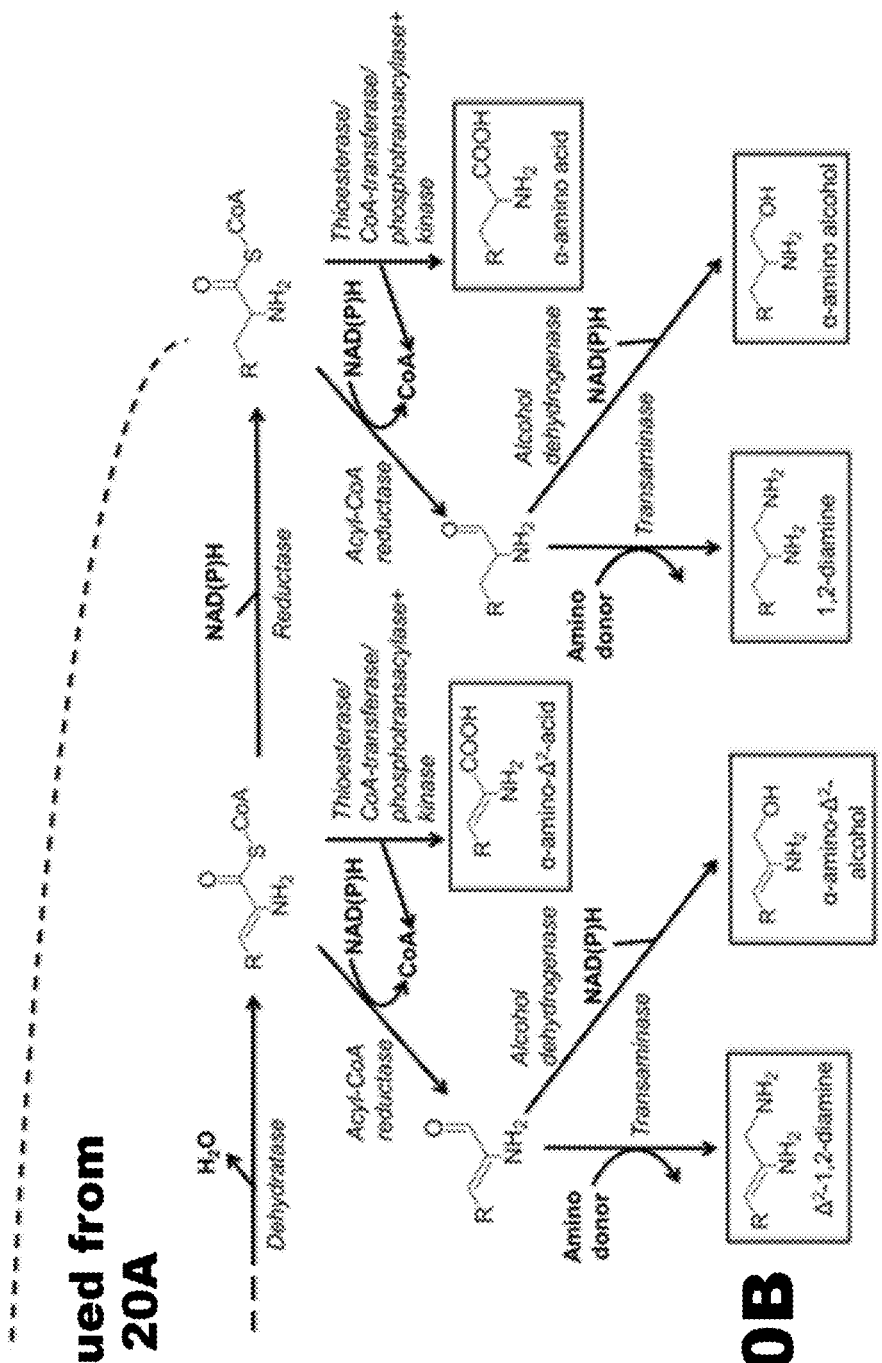
Continued from Figure 20A
FIG. 20B

FIGURE 21

A recombinant microorganism comprising overexpressed enzymes including 1) a thiolase catalyzing the condensation of an unsubstituted or functionalized acyl-CoA thioester with alpha-functionalized acetyl-CoA; a 2 hydroxyacyl-CoA dehydrogenase, 3) an enoyl-CoA hydratase, 4) an enoyl-CoA reductase and 5) a termination enzyme such as thioesterase.

A recombinant microorganism comprising an inducible expression vector or inducible integrated sequences for overexpressing enzymes including 1) a thiolase catalyzing the condensation of an unsubstituted or functionalized acyl-CoA thioester with alpha-functionalized acetyl-CoA; a 2 hydroxyacyl-CoA dehydrogenase, 3) an enoyl-CoA hydratase, 4) an enoyl-CoA reductase and 5) a termination enzyme such as thioesterase.

A recombinant microorganism being a bacteria comprising an inducible expression vector or inducible integrated sequences for overexpressing enzymes including 1) a thiolase catalyzing the condensation of an unsubstituted or functionalized acyl-CoA thioester with alpha-functionalized acetyl-CoA; a 2 hydroxyacyl-CoA dehydrogenase, 3) an enoyl-CoA hydratase, 4) an enoyl-CoA reductase and 5) a termination enzyme such as thioesterase.

A recombinant microorganism being a *E. coli* comprising an inducible expression vector or inducible integrated sequences for overexpressing enzymes including 1) a thiolase catalyzing the condensation of an unsubstituted or functionalized acyl-CoA thioester with alpha-functionalized acetyl-CoA; a 2 hydroxyacyl-CoA dehydrogenase, 3) an enoyl-CoA hydratase, 4) an enoyl-CoA reductase and 5) a termination enzyme such as thioesterase.

A genetically engineered microorganism comprising means for:
a) an overexpressed activation enzyme(s) able to produce an alpha-functionalized CoA thioester extender unit, wherein said activation enzyme is selected from:
  i) an acyl-CoA synthase which converts the alpha-functionalized CoA thioester extender unit from an alpha-functionalized acid;
  ii) an acyl-CoA transferase which converts the alpha-functionalized CoA thioester extender unit from an alpha-functionalized acid;
  iii) a phosphotransacylase and a carboxylate kinase which converts the alpha-functionalized CoA thioester extender unit from an alpha-functionalized acid;
  iv) other one or more enzymes that allow the production of the alpha-functionalized CoA thioester extender unit from the carbon source without via the alpha-functionalized acid;
b) an overexpressed activation enzyme(s) able to produce an acyl-CoA primer wherein said activation enzyme is selected from:
  i) an acyl-CoA synthase which converts the acyl-CoA primer from its acid form;
  ii) an acyl-CoA transferase which converts the acyl-CoA primer from its acid form;
  iii) a phosphotransacylase and a carboxylate kinase which converts the acyl-CoA primer from its acid form;
  iv) other one or more enzymes that allow the production of the acyl-CoA primer from the carbon source without via the alpha-functionalized acid;
c) an overexpressed thiolase enzyme that catalyzes the condensation of an acyl-CoA primer with an alpha-functionalized CoA

FIGURE 21 (CONTINUED)

thioester extender unit to form an alpha-functionalized ß-ketoacyl-CoA;

d) an overexpressed 3-hydroxyacyl-CoA dehydrogenase or 3-oxoacyl-[acyl-carrier-protein] reductase enzyme that catalyzes the reduction of said alpha-functionalized ß-ketoacyl-CoA to produce an alpha-functionalized ß-hydroxyacyl-CoA;

e) an overexpressed enoyl-CoA hydratase, 3-hydroxyacyl-CoA dehydratase, or 3-hydroxyacyl-[acyl-carrier-protein] dehydratase enzyme that catalyzes the dehydration of said alpha-functionalized ß-hydroxyacyl-CoA to an alpha-functionalized trans-enoyl-CoA;

f) an overexpressed acyl-CoA dehydrogenase, trans-enoyl-CoA reductase, or enoyl-[acyl-carrier-protein] reductase enzyme that catalyzes the reduction of said alpha-functionalized trans-enoyl-CoA to an alpha-functionalized acyl-CoA;

g) iterations of steps b to e, wherein said iteration is achieved by utilizing an alpha-functionalized acyl-CoA-thioester product generated in step e of the last turn as an primer or an extender unit of step b in the next turn of iteration;

h) an overexpressed termination enzyme(s) able to use a substrate selected from the group consisting alpha-functionalized ß-ketoacyl-CoA-thioester products generated in step b, alpha-functionalized ß-hydroxyacyl-CoA-thioester products generated in step c, alpha-functionalized trans-enoyl-CoA-thioester products generated in step d and alpha-functionalized acyl-CoA-thioester products generated in step e, wherein said termination enzyme(s) is selected from:
   i) the group consisting of a thioesterase, or an acyl-CoA transferase, or a phosphotransacylase and a carboxylate kinase catalyzing the conversion of the CoA moiety of substrate CoA thioester to a carboxylic acid group;
   ii) an aldehyde-forming acyl-CoA reductase catalyzing the conversion of the CoA moiety of a substrate to an aldehyde group and an alcohol dehydrogenase catalyzing the conversion of an aldehyde to an alcohol;
   iii) an aldehyde-forming acyl-CoA reductase catalyzing the conversion of the CoA moiety of a substrate to an aldehyde group and a transaminase catalyzing the conversion of an aldehyde to an amine;

i) optionally reduced expressions of fermentation genes leading to reduced production of lactate, acetate, ethanol and succinate; and wherein said microorganism has an iterative carbon elongation pathway beginning with said acyl-CoA thioester primer and alpha-functionalized CoA thioester extender unit and running in a biosynthetic direction.

Any microorganism as herein described, wherein said acyl-CoA primer is an acyl CoA thioester whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups.

Any microorganism as herein described, wherein said an alpha-functionalized CoA thioester extender unit is an acyl CoA thioester whose alpha group is selected from the group consisting of hydrogen, alkyl group, hydroxyl group, carboxyl group, aryl group, halogen, amino group, hydroxyacyl group, carboxyacyl group, aminoacyl group, ketoacy group, halogenated acyl group, and any other functionalized acyl groups.

Any microorganism as herein described,, wherein said alpha-functionalized acid is the acid form of alpha-functionalized CoA thioester extender unit whose omega group is selected from the group consisting of hydrogen, alkyl group, hydroxyl group, carboxyl group, aryl

FIGURE 21 (CONTINUED)

| |
|---|
| group, halogen, amino group, hydroxyacyl group, carboxyacyl group, aminoacyl group, ketoacyl group, halogenated acyl group, and any other functionalized acyl groups. |
| Any microorganism as herein described, wherein said acid form of acyl-CoA primer has omega group selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism as herein described, wherein said acid form of acyl-CoA primer is supplemented in the media or supplied through the intracellular pathway from the carbon source. |
| Any microorganism as herein described, wherein said alpha-functionalized acid is supplemented in the media or supplied through the intracellular pathway from the carbon source. |
| Any microorganism as herein described, wherein said genetically engineered microorganism produces a product selected from the group consisting of β-keto acids, β-keto alcohols, β-keto amines, β-hydroxy acids, 1,3-diols, β-hydroxy amines, $\Delta^2$-fatty acids, $\Delta^2$-fatty alcohols, $\Delta^2$-amines, fatty acids, alcohols and amines whose alpha group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism as herein described, wherein said step g uses alpha-functionalized β-ketoacyl-CoA-thioester products generated in step b as the substrate, further comprising an overexpressed β-keto acid decarboxylase catalyzing the conversion of the β-keto-acid to a ketone. |
| Any microorganism as herein described, wherein said genetically engineered microorganism produces a ketone whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism as herein described, wherein said termination pathway i) of step g uses alpha-functionalized acyl-CoA-thioester products generated in step b as the substrate, utilizing glycolyl-CoA as the extender unit and further comprising: an overexpressed keto-dehydrogenase catalyzing the conversion of a 2-hydroxy acid to an alpha-keto acid; an overexpressed alpha-keto acid decarboxylase catalyzing the conversion of an alpha-keto acid to a primary aldehyde; an overexpressed alcohol dehydrogenase catalyzing the conversion of a primary aldehyde to a primary alcohol. |
| Any microorganism as herein described, utilizing glycolyl-CoA as the extender unit and further comprising: an overexpressed 2-hydroxyacyl-CoA lyase catalyzing the conversion of a 2-hydroxyacyl-CoA, generated from step e, to a primary aldehyde and a formyl-CoA; an overexpressed alcohol dehydrogenase catalyzing the conversion of a primary aldehyde to a primary alcohol. |
| Any microorganism as herein described, wherein said genetically engineered microorganism produces a primary alcohol. |
| Any microorganism as herein described, wherein said overexpressed acyl-CoA synthase is encoded by a gene(s) selected from the group consisting of E. coli sucC, E. coli sucD, E. coli paaK, E. coli prpE, E. coli menE, E. coli fadK, E. coli fadD, Penicillium |

FIGURE 21 (CONTINUED)

| |
|---|
| chrysogenum phl, Salmonella typhimurium LT2 prpE, Bacillus subtilis bioW, Cupriavidus basilensis hmfD, Rhodopseudomonas palustris badA, R. palustris hbaA, Pseudomonas aeruginosa PAO1 pqsA, Arabidopsis thaliana 4cl and other homologs. |
| Any microorganism as herein described, wherein said overexpressed acyl-CoA transferase is encoded by a gene(s) selected from the group consisting of E. coli atoD, E. coli scpC, E. coli ydiF, E. coli atoA, E. coli atoD, Clostridium acetobutylicum ctfA, C. acetobutylicum ctfB, Clostridium kluyveri cat2, C. kluyveri cat1, P. putida pcaI, P. putida pcaJ, Megasphaera elsdenii pct, Acidaminococcus fermentans gctA, Acidaminococcus fermentans gctB, Acetobacter aceti aarC and other homologs. |
| Any microorganism as herein described, wherein said overexpressed phosphotransacylase is encoded by a gene(s) selected from the group consisting of Clostridium acetobutylicum ptb, Enterococcus faecalis ptb, Salmonella enterica pduL and other homologs. |
| Any microorganism as herein described, wherein said overexpressed carboxylate kinase is encoded by a gene(s) selected from the group consisting of Clostridium acetobutylicum buk, Enterococcus faecalis buk, Salmonella enterica pduW and other homologs. |
| Any microorganism as herein described, wherein said overexpressed thiolase is encoded by a gene(s) selected from the group consisting of E. coli atoB, E. coli yqeF, E. coli fadI, Ralstonia eutropha bktB, Pseudomonas sp. B13 catF, E. coli paaJ, Rhodococcus opacus pcaF, Pseudomonas putida pcaF, Streptomyces sp. pcaF, P. putida fadAx, P. putida fadA, Ralstonia eutropha phaA, Acinetobacter sp. ADP1 dcaF, Clostridium acetobutylicum thlA, Clostridium acetobutylicum thlB and other homologs. |
| Any microorganism as herein described, wherein said overexpressed 3-hydroxyacyl-CoA dehydrogenase or 3-oxoacyl-[acyl-carrier-protein] reductase is encoded by a gene(s) selected from the group consisting of E. coli fabG, E. coli fadB, E. coli fadJ, E. coli paaH, P. putida fadB, P. putida fadB2x, Acinetobacter sp. ADP1 dcaH, Ralstonia eutrophus phaB, Clostridium acetobutylicum hbd and other homologs. |
| Any microorganism as herein described, wherein said overexpressed enoyl-CoA hydratase, 3-hydroxyacyl-CoA dehydratase, or 3-hydroxyacyl-[acyl-carrier-protein] dehydratase is encoded by a gene(s) selected from the group consisting of E. coli fabA, E. coli fabZ, E. coli fadB, E. coli fadJ, E. coli paaF, P. putida fadB, P. putida fadB1x, Acinetobacter sp. ADP1 dcaE, Clostridium acetobutylicum crt, Aeromonas caviae phaJ and other homologs. |
| Any microorganism as herein described, wherein said acyl-CoA dehydrogenase, trans-enoyl-CoA reductase, or enoyl-[acyl-carrier-protein] reductase is encoded by a gene(s) selected from the group consisting of E. coli fadE, E. coli ydiO, Euglena gracilis TER, Treponema denticola TER, Clostridium acetobutylicum TER, E. coli fabI, Enterococcus faecalis fabK, Bacillus subtilis fabL, Vibrio cholerea fabV and other homologs. |
| Any microorganism as herein described, wherein said overexpressed thioesterase is encoded by a gene(s) selected from the group consisting of E. coli tesA, E. coli tesB, E. coli yciA, E. coli fadM, E. coli ydiI, E. coli ybgC, E. coli paaI, Mus musculus acot8, Alcanivorax borkumensis tesB2, Fibrobacter succinogenes Fs2108, Prevotella ruminicola Pr655, Prevotella ruminicola Pr1687, Lycopersicon hirsutum f glabratum mks2 and other homologs. |
| Any microorganism as herein described, wherein said overexpressed aldehyde-forming acyl-CoA reductase is encoded by a gene(s) selected from the group consisting Acinetobacter calcoaceticus acr1, Acinetobacter sp Strain M-1 acrM, Clostridium beijerinckii ald, E. coli eutE, Salmonella enterica eutE, E. coli mhpF, Clostridium kluyveri sucD and other homologs. |

FIGURE 21 (CONTINUED)

| |
|---|
| Any microorganism as herein described, wherein said overexpressed alcohol dehydrogenase is encoded by a gene(s) selected from the group consisting E. coli betA, E. coli dkgA, E. coli eutG, E. coli fucO, E. coli ucpA, E. coli yahK, E. coli ybbO, E. coli ybdH, E. coli yiaY, E. coli yigB, Saccharomyces cerevisiae ADH6, Clostridium kluyveri 4hbD, Acinetobacter sp. SE19 chnD and other homologs. |
| Any microorganism as herein described, wherein said overexpressed transaminase is encoded by a gene(s) selected from the group consisting of Arabidopsis thaliana At3g22200, Alcaligenes denitrificans aptA, Bordetella bronchiseptica BB0869, Bordetella parapertussis BPP0784, Brucella melitensis BAWG_0478, Burkholderia pseudomallei BP1026B_I0669, Chromobacterium violaceum CV2025, Oceanicola granulosus OG2516_07293, Paracoccus denitrificans PD1222 Pden_3984, Caulobacter crescentus CC_3143, Pseudogulbenkiania ferrooxidans ω-TA, Pseudomonas putida ω-TA, Ralstonia solanacearum ω-TA, Rhizobium melioti SMc01534, Vibrio fluvialis ω-TA, Bacillus megaterium SC6394 ω-TA, Mus musculus abaT, Flavobacterium lutescens lat, Streptomyces clavuligerus lat, E. coli gabT, E. coli puuE, E. coli ygjG and other homologs. |
| Any microorganism as herein described,, wherein said overexpressed β-keto acid decarboxylase is encoded by a gene(s) selected from the group consisting of Clostridium acetobutylicum adc, Lycopersicon hirsutum f glabratum mks1 and other homologs. |
| Any microorganism as herein described, wherein said overexpressed keto-dehydrogenase is encoded by a gene(s) selected from the group consisting of E. coli ldhA, E. coli lldD, E. coli leuB, Clostridium beijerinckii adh, Acidaminococcus fermentans hgdH, E. coli serA, Gordonia sp. TY-5 adh1, Gordonia sp. TY-5 adh2, Gordonia sp. TY-5 adh3, Rhodococcus ruber adh-A and other homologs. |
| Any microorganism as herein described, wherein said overexpressed alpha-keto acid decarboxylase is encoded by a gene(s) selected from the group consisting Lactococcus lactis kivd, Saccharomyces cerevisiae PDC1, S. cerevisiae PDC5, S. cerevisiae PDC6, S. cerevisiae ARO10, S. cerevisiae THI3, Zymomonas mobilis pdc and other homologs. |
| Any microorganism as herein described, wherein said overexpressed 2-hydroxyacyl-CoA lyase is encoded by a gene(s) selected from the group consisting Homo sapiens hacl1, Rattus norvegicus hacl1, Dictyostelium discoideum hacl1, Mus musculus hacl1 and other homologs. |
| Any microorganism as herein described, wherein said reduced expressions of fermentation enzymes are ΔadhE, (Δpta or ΔackA or ΔackApta), ΔpoxB, ΔldhA, and ΔfrdA and less acetate, lactate, ethanol and succinate are thereby produced. |
| Any microorganism as herein described, comprising one or more of the following mutations: fadR, atoC(c), ΔarcA, Δcrp, crp*. |
| Any microorganism herein described, said overexpressed enzymes being under the control of an inducible promoter, preferably multiple enzymes under the control of a single promoter, preferably allowing for coordinate expression of the enzymes. In one embodiment, the enzymes are expressed off an expression vector, but in another one or more are integrated into the genome. |
| A method of making alpha functionalized products, comprising growing any microorganism described herein in a nutrient broth under conditions such that said enzymes are overexpressed, said microorganism producing alpha functionalized product using said overexpressed enzymes, and isolating said alpha functionalized product. |

SEQUENCE LISTING

<160> NUMBER OF SEQ ID NOS: 46

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
aaggagatat acatatgatt gttaagccga tggtcc                              36

<210> SEQ ID NO 2
<211> LENGTH: 39
<212> TYPE: DNA
<213> ORGANISM: Artificial Sequence
<220> FEATURE:
<223> OTHER INFORMATION: Synthetic: plasmid construct

<400> SEQUENCE: 2
ttgagatctg ccatatgtta gatgcggtca aaacgttca                           39

<210> SEQ ID NO 3
<211> LENGTH: 33
<212> TYPE: DNA
<213> ORGANISM: Artificial Sequence
<220> FEATURE:
<223> OTHER INFORMATION: Synthetic: plasmid construct

<400> SEQUENCE: 3
aggagatata ccatgagcaa aggcattaaa aac                                 33

<210> SEQ ID NO 4
<211> LENGTH: 36
<212> TYPE: DNA
<213> ORGANISM: Artificial Sequence
<220> FEATURE:
<223> OTHER INFORMATION: Synthetic: plasmid construct

<400> SEQUENCE: 4
cgccgagctc gaattcttat ttcatggagc cggttt                              36

<210> SEQ ID NO 5
<211> LENGTH: 35
<212> TYPE: DNA
<213> ORGANISM: Artificial Sequence
<220> FEATURE:
<223> OTHER INFORMATION: Synthetic: plasmid construct

<400> SEQUENCE: 5
aggagatata ccatgagaaa agtagaaatc attac                               35

<210> SEQ ID NO 6
<211> LENGTH: 39
<212> TYPE: DNA
<213> ORGANISM: Artificial Sequence
<220> FEATURE:
<223> OTHER INFORMATION: Synthetic: plasmid construct

<400> SEQUENCE: 6
cgccgagctc gaattcttat tttttcagtc ccatgggac                           39

<210> SEQ ID NO 7
<211> LENGTH: 45
<212> TYPE: DNA
<213> ORGANISM: Artificial Sequence
<220> FEATURE:
<223> OTHER INFORMATION: Synthetic: plasmid construct

<400> SEQUENCE: 7
catgaaataa gaatttaagg aggaatatgg catgagcgaa ctgat                45

<210> SEQ ID NO 8
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 8
cgccgagctc gaattcttag cgtcctttaa agtcggg                         37

<210> SEQ ID NO 9
<211> LENGTH: 33
<212> TYPE: DNA
<213> ORGANISM: Artificial Sequence
<220> FEATURE:
<223> OTHER INFORMATION: Synthetic: plasmid construct

<400> SEQUENCE: 9
aggagatata ccatgcgtga agcctttatt tgt                             33

<210> SEQ ID NO 10
<211> LENGTH: 36
<212> TYPE: DNA
<213> ORGANISM: Artificial Sequence
<220> FEATURE:
<223> OTHER INFORMATION: Synthetic: plasmid construct

<400> SEQUENCE: 10
cgccgagctc gaattctcaa acacgctcca gaatca                          36

<210> SEQ ID NO 11
<211> LENGTH: 55
<212> TYPE: DNA
<213> ORGANISM: Artificial Sequence
<220> FEATURE:
<223> OTHER INFORMATION: Synthetic: plasmid construct

<400> SEQUENCE: 11
gtgtttgaga attcgaagga ggaatatacc atgatgataa atgtgcaaac tgtgg     55

<210> SEQ ID NO 12
<211> LENGTH: 44
<212> TYPE: DNA
<213> ORGANISM: Artificial Sequence
<220> FEATURE:
<223> OTHER INFORMATION: Synthetic: plasmid construct

<400> SEQUENCE: 12
cctgcaggcg cgccgagctc tcatgactca taaccgctct ccag                 44

<210> SEQ ID NO 13
<211> LENGTH: 40
<212> TYPE: DNA
<213> ORGANISM: Artificial Sequence
<220> FEATURE:
<223> OTHER INFORMATION: Synthetic: plasmid construct

<400> SEQUENCE: 13
cccaggcaag tgggccgtat ggataattca ccccaagacg                      40

```
<210> SEQ ID NO 14
<211> LENGTH: 40
<212> TYPE: DNA
<213> ORGANISM: Artificial Sequence
<220> FEATURE:
<223> OTHER INFORMATION: Synthetic: plasmid construct

<400> SEQUENCE: 14
cgtcttgggg tgaattatcc atacggccca cttgcctggg                                40

<210> SEQ ID NO 15
<211> LENGTH: 30
<212> TYPE: DNA
<213> ORGANISM: Artificial Sequence
<220> FEATURE:
<223> OTHER INFORMATION: Synthetic: plasmid construct

<400> SEQUENCE: 15
aaggagatat acatatgagc gccccggaag                                           30

<210> SEQ ID NO 16
<211> LENGTH: 42
<212> TYPE: DNA
<213> ORGANISM: Artificial Sequence
<220> FEATURE:
<223> OTHER INFORMATION: Synthetic: plasmid construct

<400> SEQUENCE: 16
ttgagatctg ccatatgtta cagcttcgat tctgagactt gc                             42

<210> SEQ ID NO 17
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 17
aaggagatat acatatgaat aaagacacac taatacc                                   37

<210> SEQ ID NO 18
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 18
ttgagatctg ccatatgtta gccggcaagt acacatc                                   37

<210> SEQ ID NO 19
<211> LENGTH: 34
<212> TYPE: DNA
<213> ORGANISM: Artificial Sequence
<220> FEATURE:
<223> OTHER INFORMATION: Synthetic: plasmid construct

<400> SEQUENCE: 19
aggagatata ccatgataac caatacaaag cttg                                      34

<210> SEQ ID NO 20
<211> LENGTH: 36
<212> TYPE: DNA
<213> ORGANISM: Artificial Sequence
<220> FEATURE:
<223> OTHER INFORMATION: Synthetic: plasmid sequence
```

<400> SEQUENCE: 20
cgccgagctc gaattctcag gcaccaacaa tattgc                                36

<210> SEQ ID NO 21
<211> LENGTH: 35
<212> TYPE: DNA
<213> ORGANISM: Artificial Sequence
<220> FEATURE:
<223> OTHER INFORMATION: Synthetic: plasmid construct

<400> SEQUENCE: 21
aaggagatat acatatgggt tttctttccg gtaag                                 35

<210> SEQ ID NO 22
<211> LENGTH: 39
<212> TYPE: DNA
<213> ORGANISM: Artificial Sequence
<220> FEATURE:
<223> OTHER INFORMATION: Synthetic: plasmid sequence

<400> SEQUENCE: 22
ttgagatctg ccatatgtta tttcagttcg agttcgttc                             39

<210> SEQ ID NO 23
<211> LENGTH: 31
<212> TYPE: DNA
<213> ORGANISM: Artificial Sequence
<220> FEATURE:
<223> OTHER INFORMATION: Synthetic: plasmid construct

<400> SEQUENCE: 23
aggagatata ccatgagcct gaatccgcgt g                                     31

<210> SEQ ID NO 24
<211> LENGTH: 38
<212> TYPE: DNA
<213> ORGANISM: Artificial Sequence
<220> FEATURE:
<223> OTHER INFORMATION: Synthetic: plasmid construct

<400> SEQUENCE: 24
cgccgagctc gaattcttaa acacgttcaa aaacggtg                              38

<210> SEQ ID NO 25
<211> LENGTH: 52
<212> TYPE: DNA
<213> ORGANISM: Artificial Sequence
<220> FEATURE:
<223> OTHER INFORMATION: Synthetic: plasmid construct

<400> SEQUENCE: 25
acgtgtttaa gaatttaagg aggaataaac catgatctat gaaggcaaag cc              52

<210> SEQ ID NO 26
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 26
cgccgagctc gaattcttag ttaaaaaagc gctgacc                               37

<210> SEQ ID NO 27

<211> LENGTH: 34
<212> TYPE: DNA
<213> ORGANISM: Artificial Sequence
<220> FEATURE:
<223> OTHER INFORMATION: Synthetic: plasmid construct

<400> SEQUENCE: 27
aggagatata ccatgctgaa cgcctatatc tatg                                34

<210> SEQ ID NO 28
<211> LENGTH: 38
<212> TYPE: DNA
<213> ORGANISM: Artificial Sequence
<220> FEATURE:
<223> OTHER INFORMATION: Synthetic: plasmid construct

<400> SEQUENCE: 28
cgccgagctc gaattcttag ctcacatttt caataacc                            38

<210> SEQ ID NO 29
<211> LENGTH: 51
<212> TYPE: DNA
<213> ORGANISM: Artificial Sequence
<220> FEATURE:
<223> OTHER INFORMATION: Synthetic: plasmid construct

<400> SEQUENCE: 29
tgtgagctaa gaatttaagg aggaataaac catgacccac ccgatcaaaa a             51

<210> SEQ ID NO 30
<211> LENGTH: 36
<212> TYPE: DNA
<213> ORGANISM: Artificial Sequence
<220> FEATURE:
<223> OTHER INFORMATION: Synthetic: plasmid construct

<400> SEQUENCE: 30
cgccgagctc gaattcttag gtggtaaagg tcagcg                              36

<210> SEQ ID NO 31
<211> LENGTH: 52
<212> TYPE: DNA
<213> ORGANISM: Artificial Sequence
<220> FEATURE:
<223> OTHER INFORMATION: Synthetic: plasmid construct

<400> SEQUENCE: 31
catgaaataa gaatttaagg aggaataaac catgattccg gatcaggata ac            52

<210> SEQ ID NO 32
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 32
cgccgagctc gaattcttat ttgccatgat agctcgg                             37

<210> SEQ ID NO 33
<211> LENGTH: 35
<212> TYPE: DNA
<213> ORGANISM: Artificial Sequence
<220> FEATURE:
<223> OTHER INFORMATION: Synthetic: plasmid construct

<400> SEQUENCE: 33
aaggagatat acatatgacc atcaccaaaa aactg                                35

<210> SEQ ID NO 34
<211> LENGTH: 38
<212> TYPE: DNA
<213> ORGANISM: Artificial Sequence
<220> FEATURE:
<223> OTHER INFORMATION: Synthetic: plasmid construct

<400> SEQUENCE: 34
ttgagatctg ccatatgtta tttgatcagc ggaacacc                             38

<210> SEQ ID NO 35
<211> LENGTH: 37
<212> TYPE: DNA
<213> ORGANISM: Artificial Sequence
<220> FEATURE:
<223> OTHER INFORMATION: Synthetic: plasmid construct

<400> SEQUENCE: 35
aaggagatat acatatgatc aacaaaacct atgagag                              37

<210> SEQ ID NO 36
<211> LENGTH: 57
<212> TYPE: DNA
<213> ORGANISM: Artificial Sequence
<220> FEATURE:
<223> OTHER INFORMATION: Synthetic: plasmid construct

<400> SEQUENCE: 36
ttggtgatgg tcatagttta ttcctcctta tttaattaaa ctgctttggc aatgctg        57

<210> SEQ ID NO 37
<211> LENGTH: 34
<212> TYPE: DNA
<213> ORGANISM: Artificial Sequence
<220> FEATURE:
<223> OTHER INFORMATION: Synthetic: plasmid sequence

<400> SEQUENCE: 37
aaggagatat acatatggag aaaagcatgt cgcc                                 34

<210> SEQ ID NO 38
<211> LENGTH: 40
<212> TYPE: DNA
<213> ORGANISM: Artificial Sequence
<220> FEATURE:
<223> OTHER INFORMATION: Synthetic: plasmid construct

<400> SEQUENCE: 38
ttgagatctg ccatatgtta tttatacttg ttagcgatgc                           40

<210> SEQ ID NO 39
<211> LENGTH: 35
<212> TYPE: DNA
<213> ORGANISM: Artificial Sequence
<220> FEATURE:
<223> OTHER INFORMATION: Synthetic: plasmid sequence

<400> SEQUENCE: 39
aaggagatat acatatgctg aaagacgagg tgatc                                35

<210> SEQ ID NO 40

<211> LENGTH: 41
<212> TYPE: DNA
<213> ORGANISM: Artificial Sequence
<220> FEATURE:
<223> OTHER INFORMATION: Synthetic: plasmid construct

<400> SEQUENCE: 40
ttgagatctg ccatatgtta tttcaggtag tcataaataa c        41

<210> SEQ ID NO 41
<211> LENGTH: 35
<212> TYPE: DNA
<213> ORGANISM: Artificial Sequence
<220> FEATURE:
<223> OTHER INFORMATION: Synthetic: plasmid construct

<400> SEQUENCE: 41
aggagatata ccatgatgac gcgtgaagtg gtagt        35

<210> SEQ ID NO 42
<211> LENGTH: 36
<212> TYPE: DNA
<213> ORGANISM: Artificial Sequence
<220> FEATURE:
<223> OTHER INFORMATION: Synthetic: plasmid construct

<400> SEQUENCE: 42
cgccgagctc gaattctcag atacgctcga agatgg        36

<210> SEQ ID NO 43
<211> LENGTH: 47
<212> TYPE: DNA
<213> ORGANISM: Artificial Sequence
<220> FEATURE:
<223> OTHER INFORMATION: Synthetic: plasmid construct

<400> SEQUENCE: 43
gcgtatctga gaattaggag gctctctatg actcagcgca ttgcgta        47

<210> SEQ ID NO 44
<211> LENGTH: 34
<212> TYPE: DNA
<213> ORGANISM: Artificial Sequence
<220> FEATURE:
<223> OTHER INFORMATION: Synthetic: plasmid construct

<400> SEQUENCE: 44
cgccgagctc gaattctcag cccatgtgca ggcc        34

<210> SEQ ID NO 45
<211> LENGTH: 32
<212> TYPE: DNA
<213> ORGANISM: Artificial Sequence
<220> FEATURE:
<223> OTHER INFORMATION: Synthetic: plasmid construct

<400> SEQUENCE: 45
aaggagatat acatatgtcg gcacaaagcc tg        32

<210> SEQ ID NO 46
<211> LENGTH: 36
<212> TYPE: DNA
<213> ORGANISM: Artificial Sequence
<220> FEATURE:
<223> OTHER INFORMATION: Synthetic: plasmid construct

```
<400> SEQUENCE: 46
ttgagatctg ccatatgtta cggcagtttc accacc                                36
```

ITERATIVE PLATFORM FOR THE SYNTHESIS OF ALPHA FUNCTIONALIZED PRODUCTS

PRIOR RELATED APPLICATIONS

This application is a continuation-in-part of U.S. Ser. No. 15/566,704 filed on Oct. 14, 2017, which is a National Phase under 35 U.S.C. § 371 of International Application PCT/US2016/027873, filed Apr. 15, 2016, which claims priority to U.S. Ser. No. 62/148,123, ITERATIVE PLATFORM FOR THE SYNTHESIS OF ALPHA FUNCTIONALIZED PRODUCTS, filed Apr. 15, 2015. All applications are expressly incorporated by reference herein in their entirety for all purposes.

FEDERALLY SPONSORED RESEARCH STATEMENT

This invention was made with government support under Grant Nos: CBET1067565 and CBET1134541 awarded by the National Science Foundation. The government has certain rights in the invention.

FIELD OF THE DISCLOSURE

This disclosure generally relates to the use of recombinant microorganisms to make various products.

BACKGROUND OF THE DISCLOSURE

Reactions that catalyze the iterative formation of carbon-carbon bonds are instrumental for many metabolic pathways, such as the biosynthesis of fatty acids, polyketides, and many other molecules with applications ranging from biofuels and green chemicals to therapeutic agents. These pathways typically start with small precursor metabolites that serve as building blocks that are subsequently condensed and modified in an iterative fashion until the desired chain length and functionality are achieved.

Most iterative carbon-carbon bond forming reactions in natural biological systems take place through a Claisen condensation mechanism in which the nucleophilic α-anion of an acyl-thioester, serving as the extender unit, attacks the electrophilic carbonyl carbon of another acyl-thioester, serving as the primer. Depending on how the nucleophilic α-anion is generated, the Claisen condensation reaction can be classified as decarboxylative or non-decarboxylative.

Many natural iterative carbon chain elongation pathways, like fatty acid and polyketide biosynthesis pathways, utilize decarboxylative Claisen condensation reactions with malonyl thioesters as extender units. Their potential products include fatty acids, alcohols, polyketides, esters, alkanes and alkenes with diverse chain lengths, structures and functionalities due to usage of functionalized primers, usage of α-functionalized malonyl thioesters as extender units and diverse pathways for termination of carbon chain elongation and subsequent product modification. However, despite the structural and functional diversity of these products, the use of malonyl thioester as a C2 extender unit requires the ATP-dependent activation of acetyl-CoA to malonyl-CoA, which in turn limits the energy efficiency of these pathways. Furthermore, owing to the decarboxylation mechanism, the β-site of extender units of the decarboxylative Claisen condensation must be a carboxylic group, restricting the range of extender units and potentially limiting the diversity of products that can be generated through these carbon chain elongation pathways.

In order to overcome this limitation, we have recently implemented a novel approach by driving beta-oxidation in reverse to make fatty acids instead of degrading them (see US20130316413, WO2013036812, each incorporated by reference in its entirety for all purposes). Unlike the fatty acid biosynthesis pathway, the reversal of the β-oxidation cycle operates with coenzyme-A (CoA) thioester intermediates and uses acetyl-CoA directly for acyl-chain elongation (rather than first requiring ATP-dependent activation to malonyl-CoA). In these pathways, thiolases catalyze the non-decarboxylative Claisen condensation in which acetyl-CoA, instead of malonyl thioesters, serves as the extender unit, and subsequent β-reduction reactions by hydroxyacyl-CoA dehydrogenases (HACDs), enoyl-CoA hydratases (ECHs) and enoyl-CoA reductases (ECRs) enable iteration. Compared to pathways utilizing decarboxylative Claisen condensation, these pathways are more energy efficient due to less ATP consumption for the supply of extender unit acetyl-CoA than malonyl thioesters. However, these thiolases only utilize acetyl-CoA as the extender unit, thus limiting the functionality of synthesized products. A novel non-decarboxylative Claisen condensation reaction able to accept wider range of extender units and proceed in an iterative manner is required to diversify the product range of carbon-chain elongation.

This disclosure demonstrates a general CoA-dependent carbon elongation platform based on the use of de novo thiolase-catalyzed non-decarboxylative Claisen condensation which accepts functionalized primers and extender units, along with suitable HACDs, ECHs and ECRs (FIG. 1) to complete one turn of the 2-carbon additive cycle. Wide-ranging product diversity (FIG. 1) from this iterative platform is achieved through the use of primers with or without functionalization (R1 in FIG. 1) and extender units with alpha-functionalization (R2 in FIG. 1) in combination with pathway termination to various product classes by multiple pathways from any intermediate with various β-reduction degrees. The proposed platform possesses the potential for the high product diversity of a biosynthetic pathway combined with the high efficiency of a fermentative pathway.

SUMMARY OF THE DISCLOSURE

This disclosure generally relates to the use of microorganisms to make alpha-functionalized chemicals and fuels, (e.g. alpha-functionalized carboxylic acids, alcohols, hydrocarbons, amines, and their beta-, and omega-functionalized derivatives), by utilizing an iterative carbon chain elongation pathway that uses functionalized extender units. The core enzymes in the pathway include thiolases, dehydrogenases, dehydratases and reductases. Native or engineered thiolases catalyze the condensation of either unsubstituted or functionalized acyl-CoA primers with an alpha-functionalized acetyl-CoA as the extender unit to generate alpha-functionalized β-keto acyl-CoA. Dehydrogenases convert alpha-functionalized β-keto acyl-CoA to alpha-functionalized β-hydroxy acyl-CoA. Dehydratases convert alpha-functionalized β-hydroxy acyl-CoA to alpha-functionalized enoyl-CoA. Reductases convert alpha-functionalized enoyl-CoA to alpha-functionalized acyl-CoA. The platform can be operated in an iterative manner (i.e. multiple turns) by using the resulting alpha-functionalized acyl-CoA as primer and either acetyl-CoA or the aforementioned alpha-functionalized extender unit in subsequent turns of the cycle. Termination pathways acting on any of the four alpha-functionalized CoA thioester intermediates terminate the platform and generate various alpha-functionalized carboxylic acids, alcohols and amines with different β-reduction degrees.

This disclosure demonstrates a general CoA-dependent carbon elongation platform based on the use of thiolase-catalyzed non-decarboxylative Claisen condensations that accept alpha-functionalized extender units, along with suitable hydroxyacyl-CoA dehydrogenases (HACDs), enoyl-CoA hydratases (ECHs) and enoyl-CoA reductases (ECRs). A wide-range of alpha-functionalized product families (e.g. alpha-functionalized carboxylic acids, alcohols, hydrocarbons, amines, and their beta-, and omega-functionalized derivatives) can be obtained through this iterative platform.

The technology entails developing a new pathway that is based on native or engineered thiolases capable of catalyzing the condensation of either unsubstituted or functionalized acyl-CoA primers with an alpha-functionalized acetyl-CoA as the extender unit. This has been reported in neither the scientific, peer-reviewed literature nor the patent literature.

The process involves performing traditional fermentations using industrial organisms (such as E. coli, S. cerevisiae) that convert different feedstocks into longer-chain products (e.g. alpha-functionalized carboxylic acids, alcohols, amines, and their beta-, and omega-functionalized derivatives or hydrocarbons). These organisms are considered workhorses of modern biotechnology. Media preparation, sterilization, inoculum preparation, and fermentation are the main steps of the process.

As used herein, a "primer" is a starting molecule for iterative carbon elongation platform. The "initial primer" or "initiating primer" can be simply acetyl-CoA or other unsubstituted or functionalized acyl-CoAs. As the chain grows by adding extender units in each cycle, the primer will accordingly increase in size.

As used herein, an "extender unit" is the donor of carbons in each cycle of the iterative carbon elongation platform. In this disclosure, the extender unit is alpha-functionalized acetyl-CoAs.

Thiolases are ubiquitous enzymes that have key roles in many vital biochemical pathways, including the beta-oxidation pathway of fatty acid degradation and various biosynthetic pathways. Members of the thiolase family can be divided into two broad categories: degradative thiolases (EC 2.3.1.16), and biosynthetic thiolases (EC 2.3.1.9). The forward and reverse reactions are shown below:

Furthermore, the degradative thiolases can be made to run in the forward direction by building up the level of left hand side reactants (primer and extender unit), thus driving the equilibrium in the forward direction and/or by overexpressing same or by expressing a mutant of same.

As used herein, a "thiolase" is an enzyme that catalyzes the condensation of an unsubstituted or functionalized acyl-CoA thioester with alpha-functionalized acetyl-CoA as the carbon donor for chain elongation to produce an unsubstituted or omega-functionalized alpha-functionalized β-keto acyl-CoA in a non-decarboxylative condensation reaction:

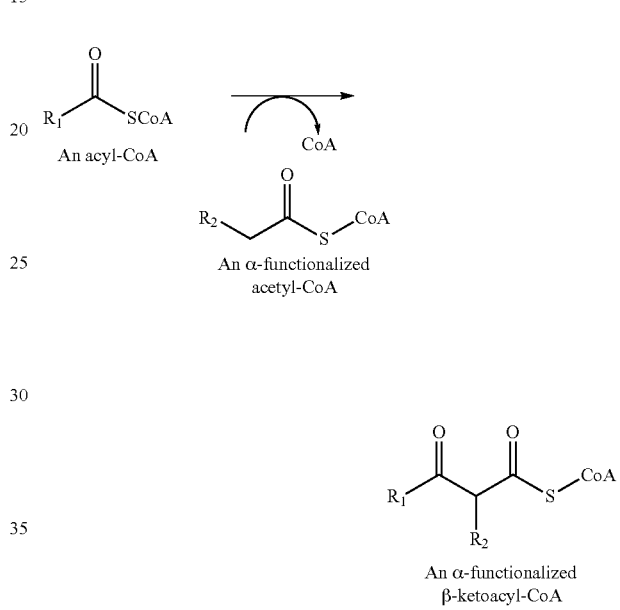

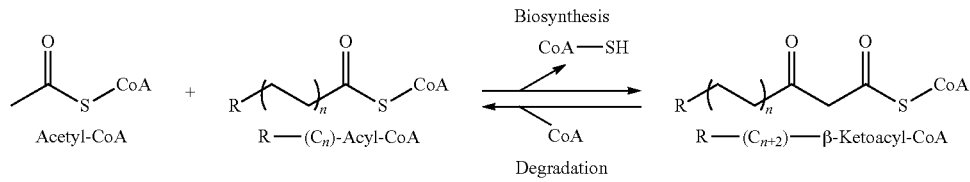

These two different types of thiolase are found both in eukaryotes and in prokaryotes: acetoacetyl-CoA thiolase (EC:2.3.1.9) and 3-ketoacyl-CoA thiolase (EC:2.3.1.16). 3-ketoacyl-CoA thiolase (also called thiolase I) has a broad chain-length specificity for its substrates and is involved in degradative pathways such as fatty acid beta-oxidation. Acetoacetyl-CoA thiolase (also called thiolase II) is specific for the thiolysis of acetoacetyl-CoA and involved in biosynthetic pathways such as poly beta-hydroxybutyric acid synthesis or steroid biogenesis.

As used herein, a "hydroxyacyl-CoA dehydrogenase" or "HACD", is an enzyme that catalyzes the reduction of an unsubstituted or omega-functionalized alpha-functionalized β-keto acyl-CoA to an unsubstituted or omega-functionalized alpha-functionalized β-hydroxy acyl-CoA:

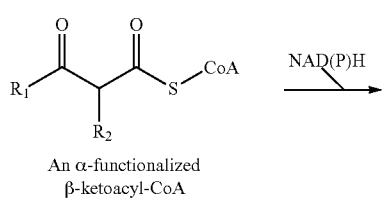

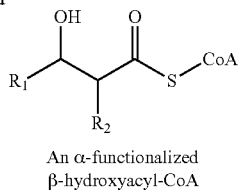

An α-functionalized
β-hydroxyacyl-CoA

As used herein, an "enoyl-CoA hydratase" or "ECH" is an enzyme that catalyzes the dehydration of an unsubstituted or omega-functionalized or alpha-functionalized β-hydroxy acyl-CoA to an unsubstituted or omega-functionalized or alpha-functionalized enoyl-CoA:

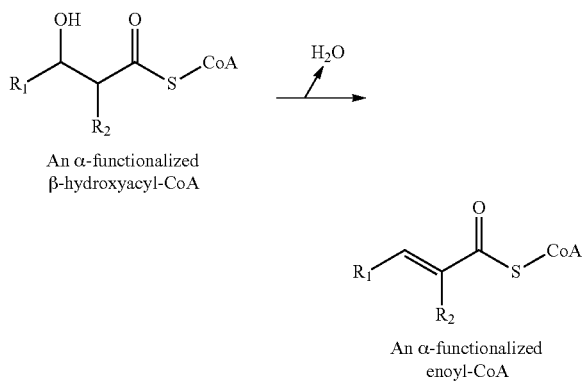

An α-functionalized
β-hydroxyacyl-CoA

An α-functionalized
enoyl-CoA

As used herein, an "enoyl-CoA reductase" or "ECR" is an enzyme that catalyzes the reduction of an unsubstituted or omega-functionalized or alpha-functionalized transenoyl-CoA to an unsubstituted or omega-functionalized of alpha-functionalized acyl-CoA:

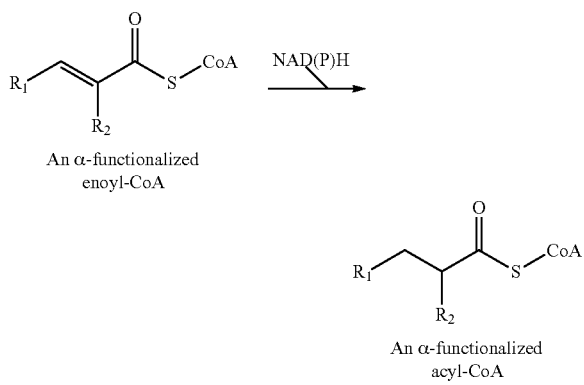

An α-functionalized
enoyl-CoA

An α-functionalized
acyl-CoA

As used herein, "termination pathway" refers to one or more enzymes (or genes encoding same) that will pull reaction CoA thioester intermediates out the iterative cycle and produce the desired end product.

As used herein, an "alpha functionalized product" is a carboxylic acid, alcohols, hydrocarbons, or amine, wherein the alpha position is the second carbon and has an R group that is not hydrogen (R preferably being e.g., alkyl, aryl, —OH, —COOH, or —X, but including others). Note that the second carbon is defined with respect to the -coA end, and the numbering is retained even when the -coA is removed. Such alpha functionalized products can be further modified herein, and thus include beta-, and omega-functionalized derivatives.

As used herein, the expressions "microorganism," "microbe," "strain" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 50% identity to one of the listed sequences and also having the same general catalytic activity, although of course Km, Kcat and the like can vary. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in E. coli, yeast, algal or other species using the codon bias for the species in which the gene will be expressed.

Initial cloning experiments have proceeded in E. coli for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List_of_sequenced_bacterial_genomes.

Additionally, yeasts, such as *Saccharomyces*, are a common species used for microbial manufacturing, and many species can be successfully transformed. Indeed, yeast are already available that express recombinant thioesterases—one of the termination enzymes described herein—and the reverse beta oxidation pathway has also been achieved in yeast. Other species include but are not limited to *Candida, Aspergillus*, Arxula adeninivorans, *Candida boidinii, Hansenula polymorpha (Pichia angusta), Kluyveromyces lactis, Pichia pastoris*, and *Yarrowia lipolytica*, to name a few.

It is also possible to genetically modify many species of algae, including e.g., *Spirulina, Aspergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) *FEMS Microbiol. Lett.* 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genetics of an organism was intentionally manipulated by the hand of man in some way.

"Reduced activity" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like. All reduced activity genes or proteins are signified herein by "−".

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any detectable expression in a species that lacks the activity altogether. Preferably, the activity is increased 100-500% or even ten fold. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids or other vectors that exist in hundreds of copies in the cell may be preferred due to its simplicity and ease of exerting externals controls, although permanent modifications to the genome may be preferred in the long term for stability reasons.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed.

"Expression vectors" are used in accordance with the art accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand of man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background mutations that do not effect the invention, and the like.

The following abbreviations are used herein:

| ABBREVIATION | TERM |
| --- | --- |
| Box-R | Beta oxidation pathway in reverse. |
| FAS | Fatty acid biosynthesis |
| ACP | Acyl carrier protein |
| CoA | Coenzyme A |
| HACD | Hydroxyacyl-CoA dehydrogenases |
| ECH | Enoyl-CoA hydratase |
| ECR | Enoyl-CoA reductase |
| HACL | 2-hydroxyacyl-CoA lyase |

BRIEF DESCRIPTION OF THE DRAWINGS

FIG. 20: Proposed platform depicted in FIG. 1 and its products utilizing phenylacetyl-CoA as the extender unit ($R_2$ in FIG. 1=—NH$_2$).

FIG. 21. A partial listing of embodiments of the invention, any one or more of which can be combined with any other.

DETAILED DESCRIPTION

This disclosure generally relates to the use of microorganisms to make alpha-functionalized chemicals and fuels, (e.g. alpha-functionalized carboxylic acids, alcohols, hydrocarbons, amines, and their beta-, and omega-functionalized derivatives), by utilizing a novel iterative carbon chain elongation pathway that uses functionalized extender units to grow a carbon chain by two carbon units.

The core enzymes in the pathway include thiolase, dehydrogenase, dehydratase and reductase. Native or engineered thiolases catalyze the condensation of either unsubstituted or functionalized acyl-CoA primers with an alpha-functionalized acetyl-CoA as the extender unit to generate alpha-functionalized β-keto acyl-CoA. Dehydrogenase converts alpha-functionalized β-keto acyl-CoA to alpha-functionalized β-hydroxy acyl-CoA. Dehydratase converts alpha-functionalized β-hydroxy acyl-CoA to alpha-functionalized enoyl-CoA. Reductase converts alpha-functionalized enoyl-CoA to alpha-functionalized acyl-CoA.

Figure 1A:
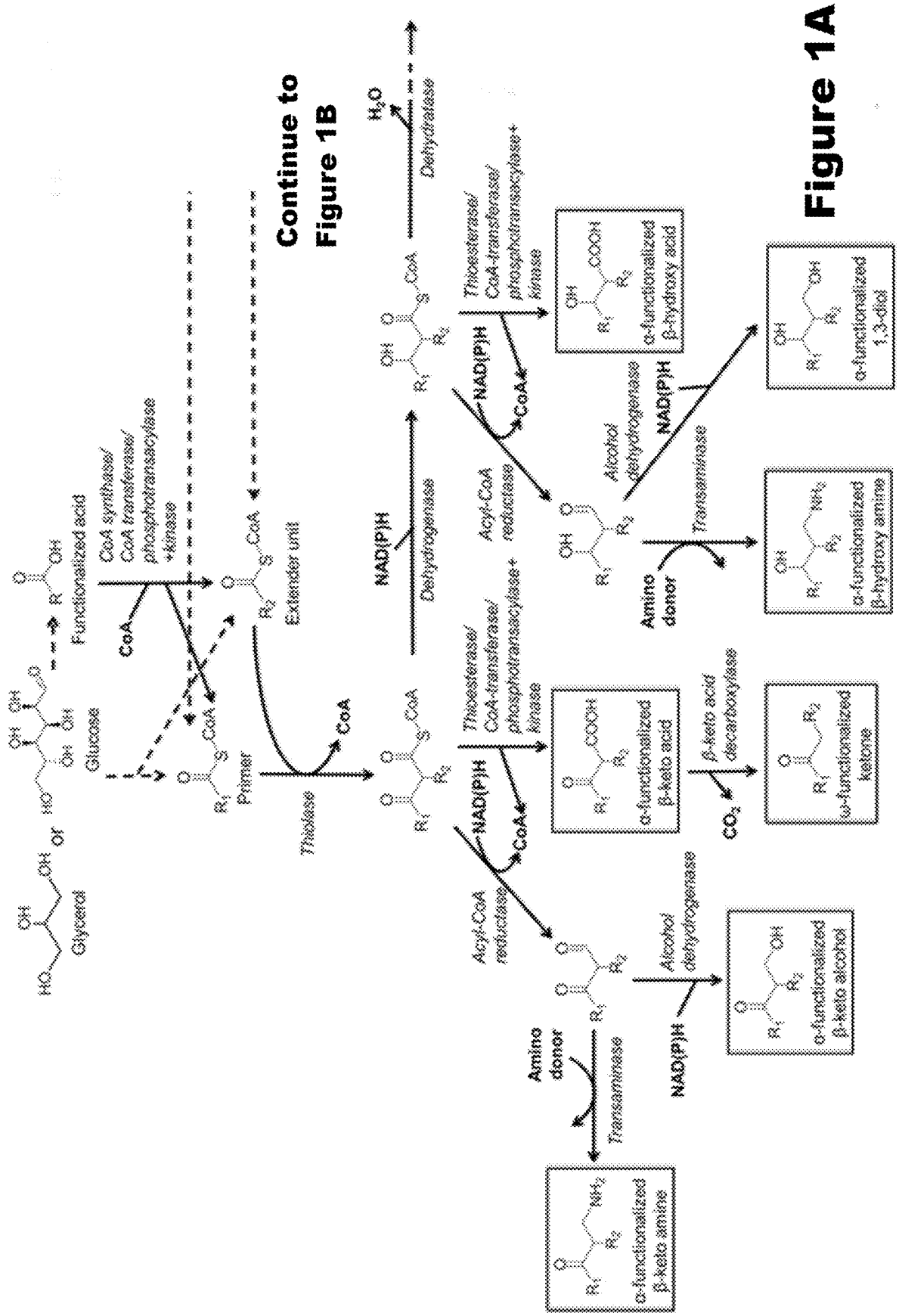
FIG. 1: Platform for the synthesis of alpha-functionalized carboxylic acids, alcohols and amines. Acyl-CoA primer, which is either unsubstituted or functionalized, and alpha-functionalized extender unit are mainly activated from their acid form, which can be either supplemented in the media or derived from carbon sources. Primer and extender unit can also be derived from carbon sources without the need to generate their acid forms. The platform is composed of thiolases, dehydrogenases, dehydratases and reductases. Thiolases catalyze a condensation between acyl-CoA primer and alpha-functionalized acyl-CoA extender and generates alpha-functionalized β-keto acyl-CoA. Dehydrogenases convert alpha-functionalized β-keto acyl-CoA to alpha-functionalized β-hydroxy acyl-CoA. Dehydratases convert alpha-functionalized β-hydroxy acyl-CoA to alpha-functionalized enoyl-CoA. Reductases convert alpha-functionalized enoyl-CoA to alpha-functionalized acyl-CoA. Iterative operation can be realized by using alpha-functionalized acyl-CoA as primer and either acetyl-CoA or alpha-functionalized acetyl-CoA as extender unit in subsequent turns of the platform. Termination pathways starting from four alpha-functionalized CoA thioester intermediates terminate the platform and generate various alpha-functionalized carboxylic acids, alcohols and amines with different β-reduction degrees. There are three types of termination pathways: thioesterase/CoA-transferase/phosphotransacylase+kinase, which generates carboxylic acids; acyl-CoA reductase and alcohol dehydrogenase which generate alcohols; acyl-CoA reductase and transaminase which generate amine. $R_1$ and $R_2$ mean functionalized group from primer and extender unit respectively. Dashed line means multiple reaction steps or iteration.
Figure 1B:
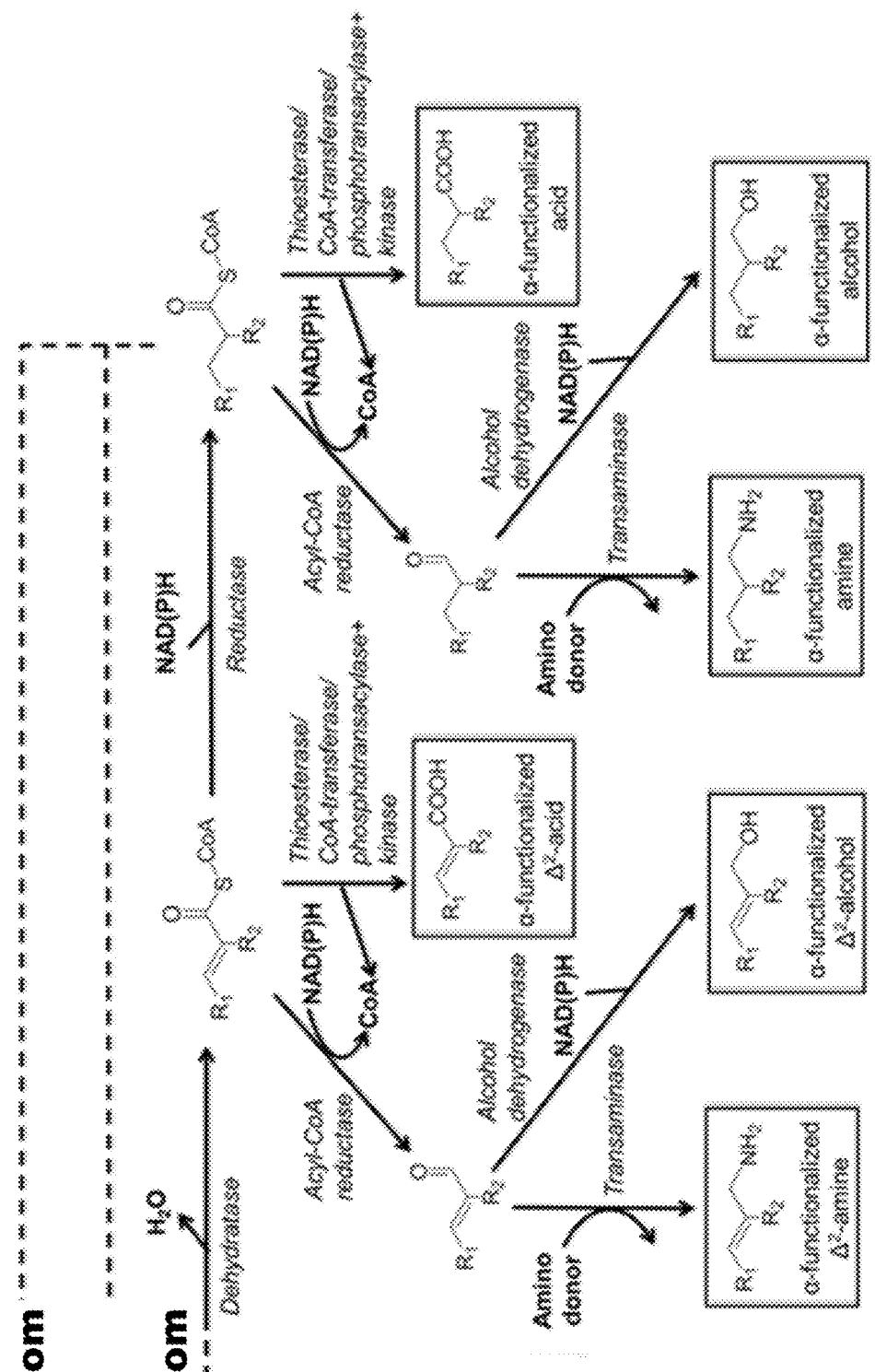
Figure 1B:
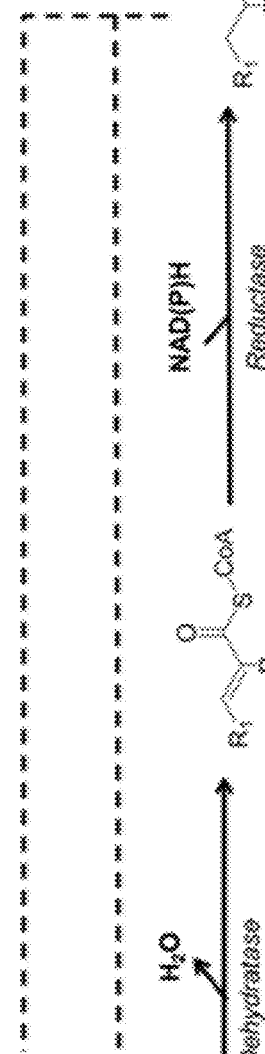
Figure 2A:
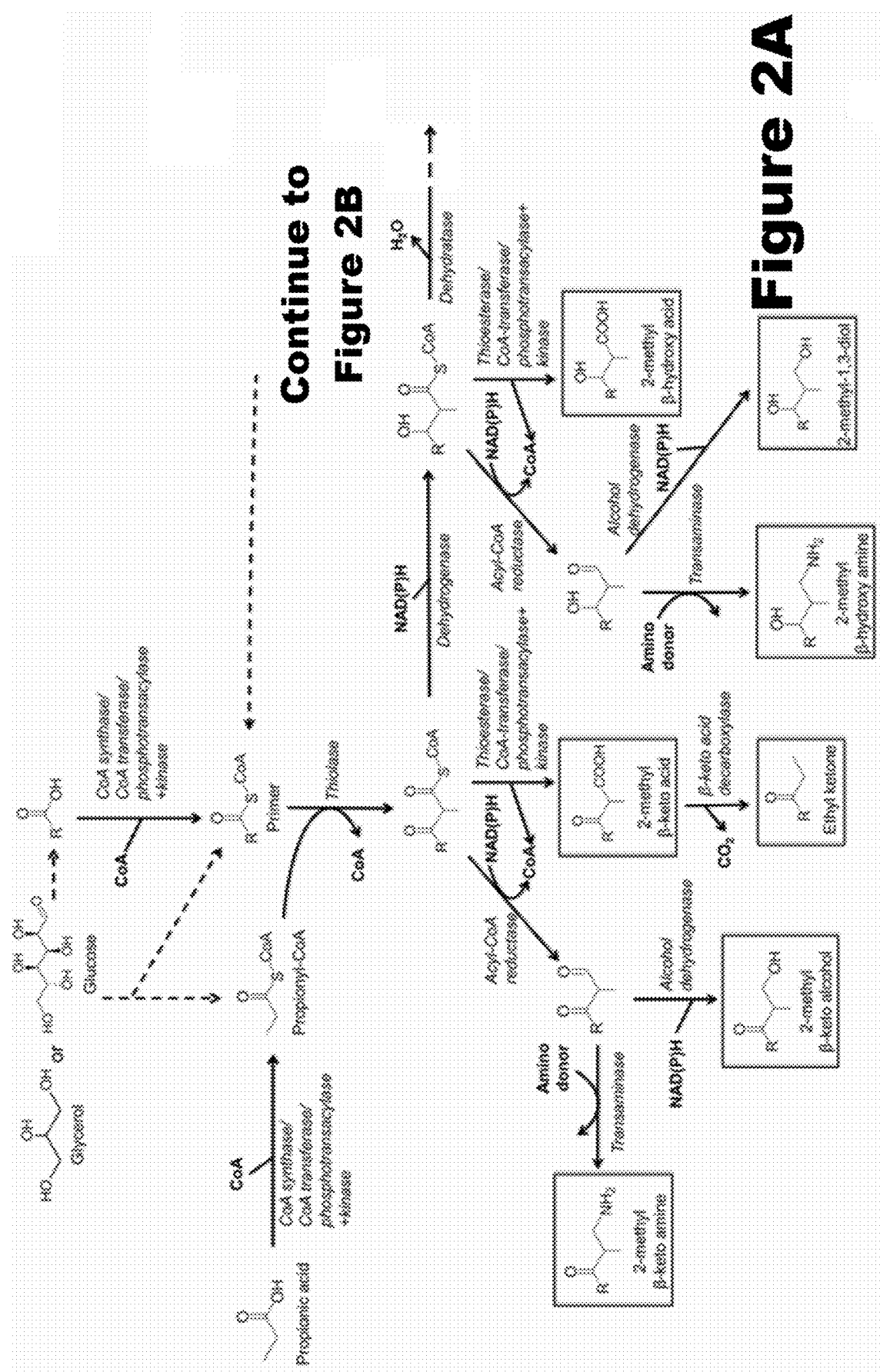
FIG. 2: Proposed platform depicted in FIG. 1 and its products utilizing propionyl-CoA as the extender unit ($R_2$ in FIG. 1=—$CH_3$).
Figure 2B:
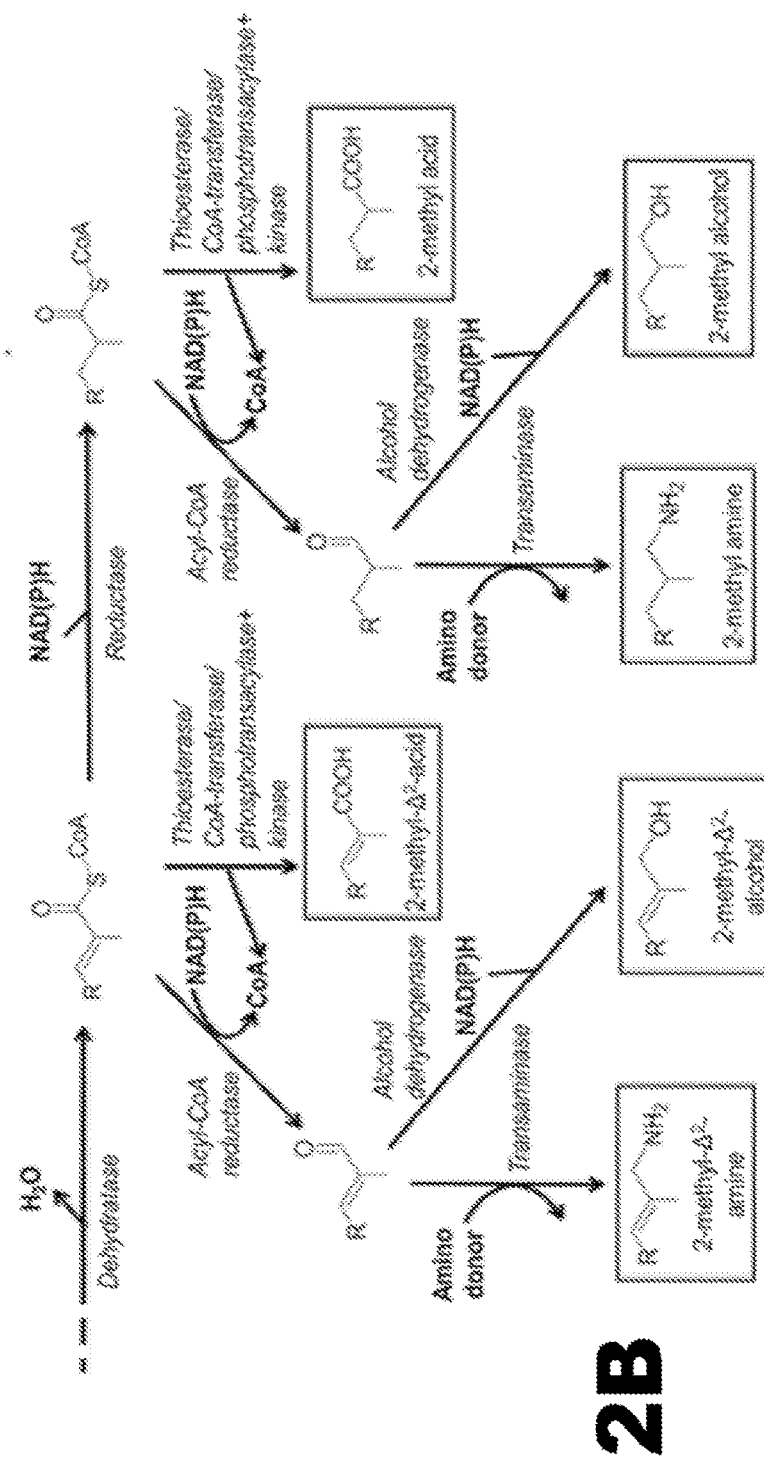
Figure 3:
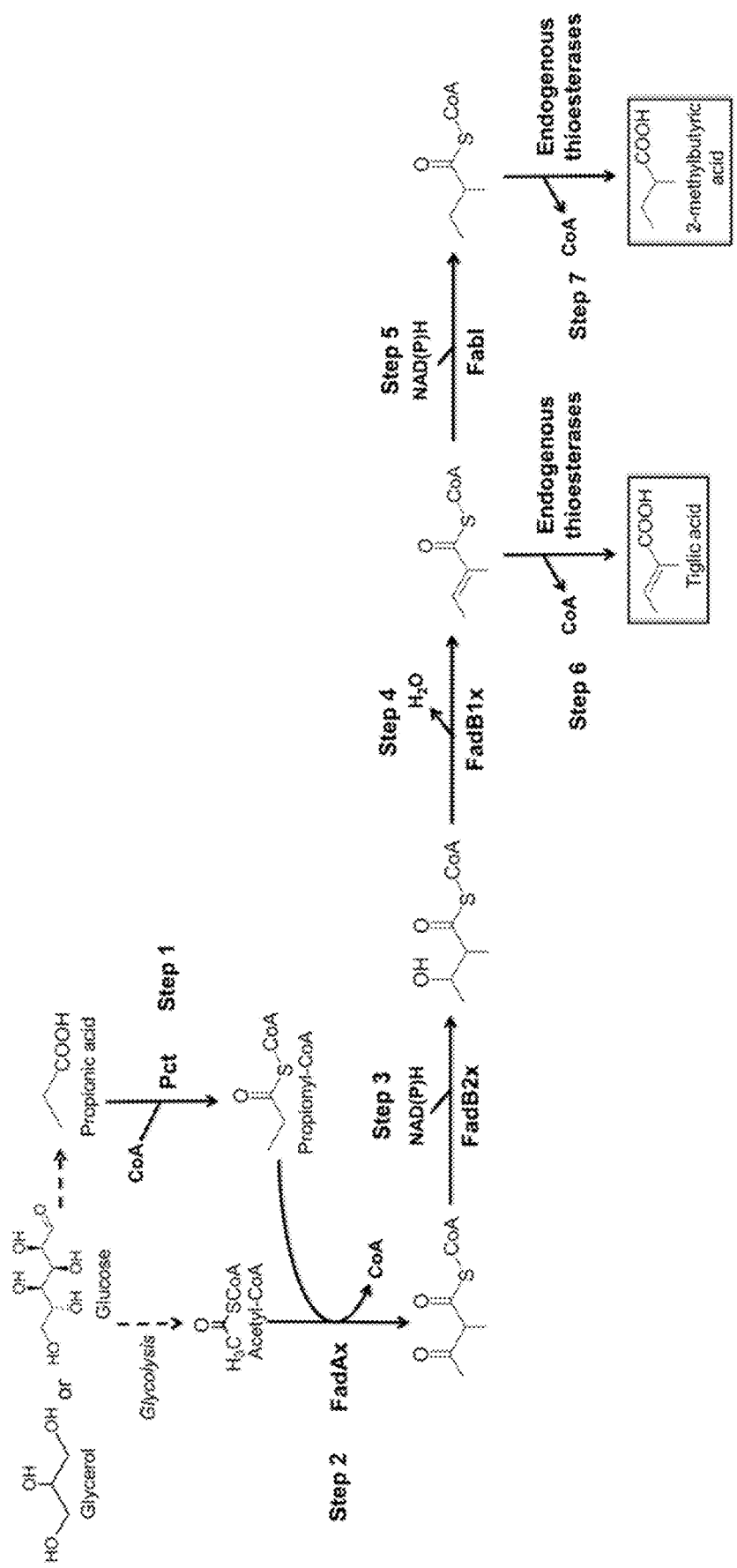
FIG. 3: Example pathway of synthesis of tiglic acid (trans-2-methyl-2-butenoic acid) and 2-methylbutyric acid through the proposed platform with acetyl-CoA as the primer and propionyl-CoA as the extender unit. Propionyl-CoA is activated by Pct from propionic acid (Step 1). The platform is composed of thiolase FadAx, which catalyzes the condensation between primer acetyl-CoA and extender unit propionyl-CoA to 2-methyl acetoacetyl-CoA (Step 2); dehydrogenase FadB2x, which converts 2-methyl acetoacetyl-CoA to 2-methyl-3-hydroxybutyryl-CoA (Step 3); dehydratase FadB1x, which converts 2-methyl-3-hydroxybutyryl-CoA to tiglyl-CoA (Step 4); reductase FabI, which reduces tiglyl-CoA to 2-methylbutyryl-CoA (Step 5). Termination reactions by endogenous thioesterases from tiglyl-CoA (Step 6) and 2-methylbutyryl-CoA (Step 7) finally generate products tiglic acid and 2-methylbutyric acid.
Figure 4:
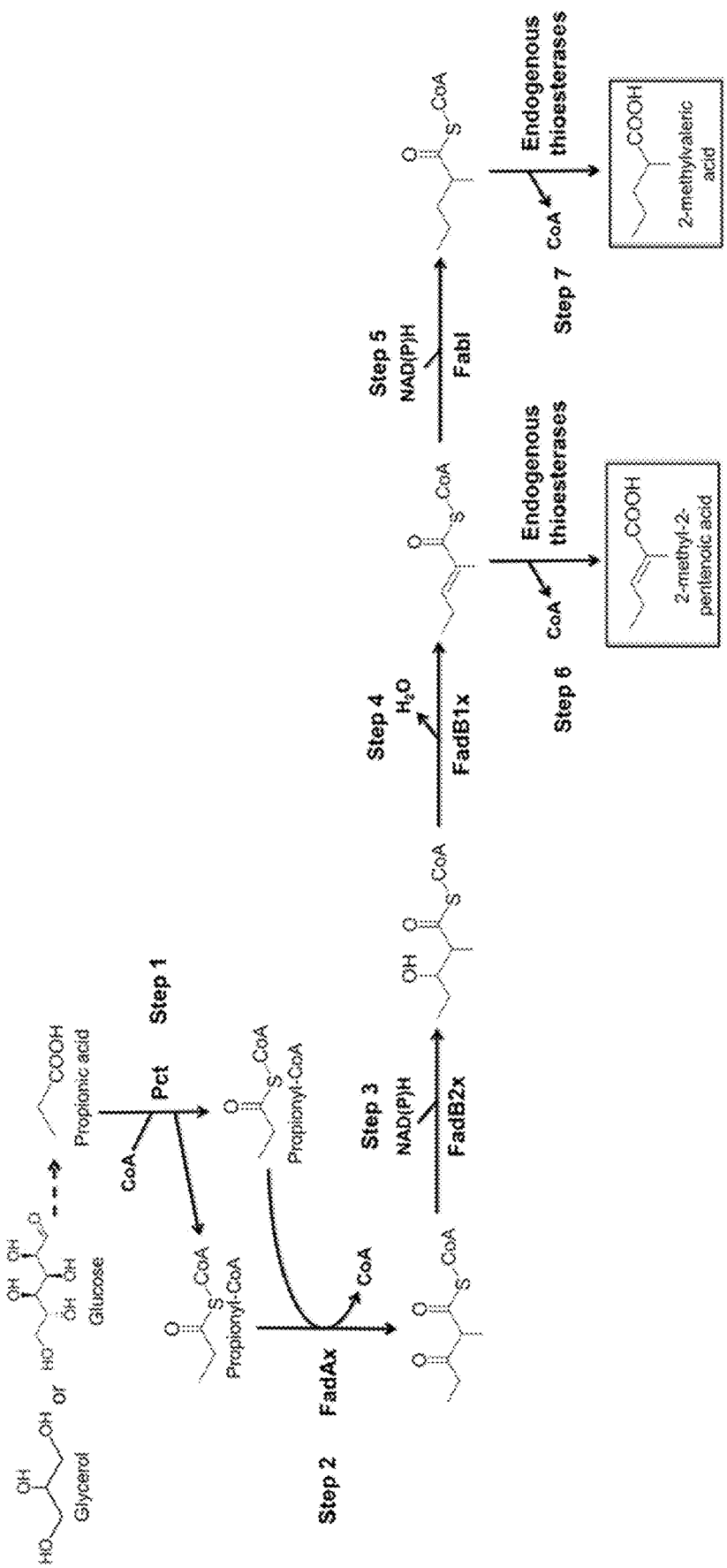
FIG. 4: Example pathway of synthesis of trans-2-methyl-2-pentenoic acid and 2-methylvaleric acid through the proposed platform with propionyl-CoA as the primer and the extender unit. Propionyl-CoA is activated by Pct from propionic acid (Step 1). The platform is composed of thiolase FadAx, which catalyzes the condensation between two molecules of propionyl-CoA to 2-methyl-3-oxopentanoyl-CoA (Step 2); dehydrogenase FadB2x, which converts 2-methyl-3-oxopentanoyl-CoA to 2-methyl-3-hydroxypentanoyl-CoA (Step 3); dehydratase FadB1x, which converts 2-methyl-3-hydroxypentanoyl-CoA to 2-methyl pentenoyl-CoA (Step 4); reductase FabI, which reduces 2-methyl-2-pentenoyl-CoA to 2-methylvaleryl-CoA (Step 5). Termination reactions by endogenous thioesterases from 2-methyl-2-pentenoyl-CoA (Step 6) and 2-methylvaleryl-CoA (Step 7) finally generate products 2-methyl-2-pentenoic acid and 2-methylvaleric acid.

The platform can be operated in an iterative manner (i.e. multiple turns) by using the resulting alpha-functionalized acyl-CoA as primer and the aforementioned omega-functionalized extender unit in subsequent turns of the cycle. Various termination pathways (FIG. 1 and Table 4) acting on any of the four alpha-functionalized CoA thioester intermediates terminate the platform and generate various alpha-functionalized carboxylic acids, alcohols and amines with different β-reduction degrees.

Thioesterase or CoA transferase or phosphotransacylase+ carboxylate kinase can terminate the platform by converting the alpha-functionalized acyl-CoAs to alpha-functionalized carboxylic acids. If alpha-functionalized carboxylic acids has keto group at the beta-site, it can then be converted to ketone through reactions by beta-keto acid decarboxylase. Acyl-CoA reductases can terminate the platform by converting the alpha-functionalized acyl-CoAs to alpha-functionalized aldehydes. Alpha-functionalized aldehydes can then be converted to alpha-functionalized alcohols and alpha-functionalized amines through reactions by alcohol dehydrogenase and transaminase respectively.

This disclosure also relates to a novel primary alcohol synthesis incorporating the proposed iterative platform using glycolyl-CoA (alpha-hydroxy acetyl-CoA) as the extender unit. When the platform uses glycolyl-CoA as the extender unit, it generates alpha-hydroxyacyl-CoA, which can be converted to primary alcohol by termination pathways selected from: a) 2-hydroxyacyl-CoA lyase (HACL) that converts alpha-hydroxyacyl-CoA to primary aldehyde with one less carbon and formyl-CoA, and alcohol dehydrogenase subsequently converts the primary aldehyde to primary alcohol; b) acid-forming termination enzyme selected from thioesterase, CoA transferase and phosphotransacylase+carboxylate kinase that converts alpha-hydroxyacyl-CoA to alpha-hydroxy acid, keto-dehydrogenase that converts alpha-hydroxy acid to alpha-keto acid, alpha-keto acid decarboxylase that converts alpha-keto acid to primary aldehyde with one less carbon and alcohol dehydrogenase subsequently converts the primary aldehyde to primary alcohol.

Many examples of thiolase enzymes which can potentially catalyze the non-decarboxylative condensation of an acyl-CoA primer and acetyl-CoA extender unit are provided herein and Table 1 provides several additional examples which can also serve as templates for engineered variants:

TABLE 1

Example Thiolase Enzymes (EC Number 2.3.1.—)

| Source organism and gene name | Protein Accession Numbers |
| --- | --- |
| E. coli atoB | NP_416728.1 |
| E. coli yqeF | NP_417321.2 |
| E. coli fadA | YP_026272.1 |
| E. coli fadI | NP_416844.1 |
| Streptomyces collinus fadA | Q93C88 |
| Ralstonia eutropha bktB | AAC38322.1 |
| Pseudomonas sp. Strain B13 catF | AAL02407.1 |
| E coli paaJ | NP_415915.1 |
| Pseudomonas putida pcaF | AAA85138.1 |
| Rhodococcus opacus pcaF | YP_002778248.1 |
| Streptomyces sp. pcaF | AAD22035.1 |
| Ralstonia eutropha phaA | AEI80291.1 |
| Clostridium acetobutylicum thlA | AAC26023.1 |
| Clostridium acetobutylicum thlB | AAC26026.1 |

This technology takes the above thiolase initiated pathway one step further to make alpha functionalized products. The method entails developing a new pathway that is based on native or engineered thiolases capable of catalyzing the condensation of either unsubstituted or functionalized acyl-CoA primers with an omega-functionalized acetyl-CoA as the extender unit. This has been reported in neither the scientific, peer-reviewed literature nor the patent literature.

Materials that can be used with the invention include those in Tables 2-5 below.

TABLE 2

Activation enzymes

| Reaction | Illustration | EC Numbers | Enzyme names | Source organism and gene name | Protein Accession Numbers |
| --- | --- | --- | --- | --- | --- |
| Carboxylic acid → Acyl-CoA (including acyl-CoA primer, and α-functionalized acetyl-CoA acting as the extender unit) | R−C(=O)−OH (A carboxylic acid) → R−C(=O)−S−CoA (An acyl-CoA) | 6.2.1.- | Acyl-CoA synthetase | E. coli paaK | NP_415916.1 |
| | | | | E. coli sucCD | NP_415256.1 |
| | | | | | NP_415257.1 |
| | | | | E. coli fadK | NP_416216.4 |
| | | | | E. coli fadD | NP_416319.1 |
| | | | | E. coli prpE | NP_414869.1 |
| | | | | E. coli menE | NP_416763.1 |
| | | | | Penicillium chrysogenum phl | CAJ15517.1 |
| | | | | Salmonella typhimurium LT2 prpE | AAL19325.1 |
| | | | | Bacillus subtilis bioW | AAC00261.1 |
| | | | | Cupriavidus basilensis hmfD | ADE20402.1 |
| | | | | Rhodopseudomonas palustris badA | CAJ18317.1 |
| | | | | R. palustris hbaA | CAE26113.1 |
| | | | | Pseudomonas aeruginosa PAO1 pqsA | NP_249687.1 |
| | | | | Arabidopsis thaliana 4cl | Q42524.1 |
| | | 2.8.3- | CoA transferase | E. coli atoD | NP_416725.1 |
| | | | | E. coli atoA | NP_416726.1 |
| | | | | E. coli scpC | NP_417395.1 |
| | | | | Clostridium kluyveri cat1 | AAA92346.1 |
| | | | | Clostridium kluyveri cat2 | AAA92344.1 |
| | | | | Clostridium acetobutylicum ctfAB | NP_149326.1, NP_149327.1 |
| | | | | Pseudomonas putida pcaIJ | NP_746081.1, NP_746082.1 |
| | | | | Megasphaera elsdenii pct | WP_014015705.1 |

TABLE 2-continued

| | | | | | |
|---|---|---|---|---|---|
| | | Activation enzymes | | | |
| Reaction | Illustration | EC Numbers | Enzyme names | Source organism and gene name | Protein Accession Numbers |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | 2.3.1.-; 2.7.2.1; 2.7.2.15 | Phospho-transacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |

TABLE 3

| | | | | | |
|---|---|---|---|---|---|
| | | Reactions of the platform | | | |
| Reaction | Illustration | EC Numbers | Enzyme names | Source organism and gene name | Protein Accession Numbers |
| Acyl-CoA + α-functionalized acetyl-CoA → α-functionalized β-ketoacyl-CoA | | 2.3.1.- | Thiolase | *E. coli* atoB | NP_416728.1 |
| | | | | *E. coli* yqeF | NP_417321.2 |
| | | | | *E. coli* fadA | YP_026272.1 |
| | | | | *E. coli* fadI | NP_4168441 |
| | | | | *Ralstonia eutropha* bktB | AAC38322.1 |
| | | | | *Pseudomonas* sp. Strain B13 catF | AAL02407.1 |
| | | | | *E coli* paaJ | NP_415915.1 |
| | | | | *Pseudomonas putida* pcaF | AAA85138.1 |
| | | | | *Rhodococcus opacus* pcaF | YP_002778248.1 |
| | | | | *Streptomyces* sp. pcaF | AAD22035.1 |
| | | | | *Ralstonia eutropha* phaA | AEI80291.1 |
| | | | | *Clostridium acetobutylicum* thlA | AAC26023.1 |
| | | | | *Clostridium acetobutylicum* thlB | AAC26026.1 |
| | | | | *Pseudomonas putida* fadA | AAK18168.1 |
| | | | | *P. putida* fadAx | AAK18171.1 |
| | | | | *Acinetobacter* sp. ADP1 dcaF | CAG68532.1 |
| | | | | *E. coli* paaJ | NP_415915.1 |
| α-functionalized β-ketoacyl-CoA → α-functionalized β-hydroxyacyl-CoA | | 1.1.1.35; 1.1.1.36 | Hydroxyacyl-CoA dehydrogenase | *E. coli* fadB | NP_418288.1 |
| | | | | *E. coli* fadJ | NP_416843.1 |
| | | | | *E. coli* paaH | NP_415913.1 |
| | | | | *P. putida* fadB | AAK18167.2 |
| | | | | *P. putida* fadB2x | AAK18170.1 |
| | | | | *Acinetobacter* sp. ADP1 dcaH | CAG68533.1 |
| | | | | *Ralstonia eutrophus* phaB | P14697.1 |
| | | | 3-oxoacyl-[acyl-carrier-protein] reductase | *Clostridium acetobutylicum* hbd | AAA95971.1 |
| | | | | *E. coli* fabG | NP_415611.1 |

TABLE 3-continued

Reactions of the platform

| Reaction | Illustration | EC Numbers | Enzyme names | Source organism and gene name | Protein Accession Numbers |
|---|---|---|---|---|---|
| α-functionalized β-hydroxyacyl-CoA → α-functionalized enoyl-CoA | (structure: β-hydroxyacyl-CoA → enoyl-CoA + H₂O) | 4.2.1.17; 4.2.1.119 | enoyl-CoA hydratase | E. coli fadB | NP_418288.1 |
| | | | | E. coli fadJ | NP_416843.1 |
| | | | | E. coli paaF | NP_415911.1 |
| | | | | P. putida fadB | AAK18167.2 |
| | | | | P. putida fadBlx | AAK18173.1 |
| | | | | Acinetobacter sp. ADP1 dcaE | CAG68535.1 |
| | | | | Clostridium acetobutylicum crt | AAA95967.1 |
| | | | | 3-hydroxyacyl-[acyl-carrier-protein] dehydratase | Aeromonas caviae phaJ | 032472.1 |
| | | | | E. coli fabA | NP_415474.1 |
| | | | | E. coli fabZ | NP_414722.1 |
| α-functionalized enoyl-CoA → α-functionalized acyl-CoA | (structure: enoyl-CoA + NAD(P)H → acyl-CoA) | 1.3.1.44 | enoyl-CoA reductase | Euglena gracilis TER | Q5EU90.1 |
| | | | | Treponema denticola TER | 4GGO_A |
| | | | | Clostridium acetobutylicum TER | 4EUH_A |
| | | | enoy-[acyl-carrier-protein] reductase | E. coli fabI | NP_415804.1 |
| | | | | Enterococcus faecalis fabK | NP_816503.1 |
| | | | | Bacillus subtilis fabL | KFK80655.1 |
| | | | | Vibrio cholerae fabV | ABX38717.1 |
| | | | acyl-CoA dehydrogenase | E. coli fadE | NP_414756.2 |
| | | | | E. coli ydiO | NP_416210.4 |

TABLE 4

Termination Pathways

| Reaction | Illustration | EC Numbers | Enzyme names | Source organism and gene name | Protein Accession Numbers |
|---|---|---|---|---|---|
| Acyl-CoA → Carboxylic acid | An acyl-CoA → A carboxylic acid | 3.1.2.- | Thioesterase | E. coli tesA | NP_415027.1 |
| | | | | E. coli tesB | NP_414986.1 |
| | | | | E. coli yciA | NP_415769.1 |
| | | | | E. coli fadM | NP_414977.1 |
| | | | | E. coli ydiI | NP_416201.1 |
| | | | | E. coli ybgC | NP_415264.1 |
| | | | | E. coli paaI | NP_415914.1 |
| | | | | Mus musculus acot8 | P58137.1 |
| | | | | Lycopersicon hirsutum f glabratum mks2 | ADK38536.1 |
| | | | | Alcanivorax borkumensis tesB2 | YP_692749.1 |
| | | | | Fibrobacter succinogenes Fs2108 | YP_005822012.1 |
| | | | | Prevotella ruminicola Pr655 | YP_003574018.1 |
| | | | | Prevotella ruminicola Pr1687 | YP_003574982.1 |
| | | 2.8.3- | CoA transferase | E. coli atoD | NP_416725.1 |
| | | | | E. coli atoA | NP_416726.1 |
| | | | | E. coli scpC | NP_417395.1 |
| | | | | Clostridium kluyveri cat1 | AAA92346.1 |
| | | | | Clostridium kluyveri cat2 | AAA92344.1 |

TABLE 4-continued

Termination Pathways

| Reaction | Illustration | EC Numbers | Enzyme names | Source organism and gene name | Protein Accession Numbers |
|---|---|---|---|---|---|
| | | | | *Clostridium acetobutylicum* ctfAB | NP_149326.1, NP_149327.1 |
| | | | | *Pseudomonas putida* pcaIJ | NP_746081.1 NP_746082.1 |
| | | | | *Megasphaera elsdenii* pct | WP_014015705.1 |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | 2.3.1.-; 2.7.2.1; 2.7.2.15 | Phospho-transacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| Acyl-CoA→ Aldehyde | An acyl-CoA → An aldehyde | 1.2.1.10 | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| | | | | *Salmonella enterica* eutE | AAA80209.1 |
| | | | | *Marinobacter aquaeolei* VT8 maqu_2507 | YP_959769.1 |
| | | | | *E. coli* mhpF | NP_414885.1 |
| | | | | *Clostridium kluyveri* sucD | EDK35023.1 |
| Aldehyde→ Alcohol | An aldehyde → An alcohol | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| | | | | *Acinetobacter* sp. SE19 chnD | AAG10028.1 |
| Aldehyde→ Amine | An aldehyde → An amine | 2.6.1.- | Transaminase | *Arabidopsis thaliana* At3g22200 | NP_001189947.1 |
| | | | | *Alcaligenes denitrificans* AptA | AAP92672.1 |
| | | | | *Bordetella bronchiseptica* BB0869 | WP_015041039.1 |
| | | | | *Bordetella parapertussis* BPP0784 | WP_010927683.1 |

TABLE 4-continued

Termination Pathways

| Reaction | Illustration | EC Numbers | Enzyme names | Source organism and gene name | Protein Accession Numbers |
|---|---|---|---|---|---|
| | | | | *Brucella melitensis* BAWG_0478 | EEW88370.1 |
| | | | | *Burkholderia pseudomallei* BP102613_I0669 | AFI65333.1 |
| | | | | *Chromobacterium violaceum* CV2025 | AAQ59697.1 |
| | | | | *Oceanicola granulosus* OG2516_07293 | WP_007254984.1 |
| | | | | *Paracoccus denitrificans* PD1222 Pden_3984 | ABL72050.1 |
| | | | | *Pseudogulbenkiania ferrooxidans* ω-TA | WP_008952788.1 |
| | | | | *Pseudomonas putida* ω-TA | P28269.1 |
| | | | | *Ralstonia solanacearum* ω-TA | YP_002258353.1 |
| | | | | *Rhizobium meliloti* SMc01534 | NP_386510.1 |
| | | | | *Vibrio fluvialis* ω-TA | AEA39183.1 |
| | | | | *Mus musculus* abaT | AAH58521.1 |
| | | | | *Flavobacterium lutescens* lat | BAB13756.1 |
| | | | | *Streptomyces clavuligerus* lat | AAB39899.1 |
| | | | | *E. coli* gabT | YP_490877.1 |
| | | | | *E. coli* puuE | NP_415818.1 |
| | | | | *E. coli* ygjG | NP_417544.5 |
| β-keto acid → ketone | 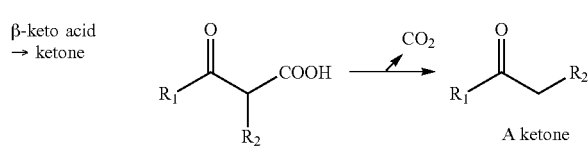 | 4.1.1.56; | β-keto acid decarboxylase | *Lycopersicon hirsutum* f glabratum mks1 | ADK38535.1 |
| | | | | *Clostridium acetobutylicum* adc | AAA63761.1 |

TABLE 5

Enzymes for derivatization of 2-hydroxy acid to primary alcohol

| Reaction | Illustration | EC Numbers | Enzyme names | Source organism and gene name | Protein Accession Numbers |
|---|---|---|---|---|---|
| 2-hydroxy acid → α-keto acid | 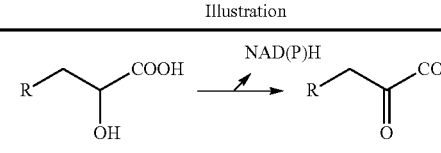 | 1.1.1- | Keto-dehydrogenase | *Clostridium beijerinckii* adh | AAA23199.2 |
| | | | | *E. coli* serA | NP_417388.1 |
| | | | | *Gordonia* sp. TY-5 adh1 | BAD03962.1 |
| | | | | *Gordonia* sp. TY-5 adh2 | BAD03964.1 |
| | | | | *Gordonia* sp. TY-5 adh3 | BAD03961.1 |

TABLE 5-continued

Enzymes for derivatization of 2-hydroxy acid to primary alcohol

| Reaction | Illustration | EC Numbers | Enzyme names | Source organism and gene name | Protein Accession Numbers |
|---|---|---|---|---|---|
| | | | | Rhodococcus ruber adh-A | WP_043801412.1 |
| | | | | Acidaminococcus fermentans hgdH | ADB47349.1 |
| | | | | E. coli ldhA | NP_415898.1 |
| | | | | E. coli lldO | NP_418062.1 |
| | | | | E. coli leuB | NP_414615.4 |
| α-keto acid → primary aldehyde | An α-keto acid → A primary aldehyde + CO$_2$ | 4.1.1.1 | α-keto acid decarboxylase | Lactococcus lactis kivd | AIS03677.1 |
| | | | | Saccharomyces cerevisiae PDC1 | CAA97573.1 |
| | | | | S. cerevisiae PDC5 | CAA97705.1 |
| | | | | S. cerevisiae PDC6 | CAA97089.1 |
| | | | | S. cerevisiae ARO10 | NP_010668.3 |
| | | | | S. cerevisiae THI3 | CAA98646.1 |
| | | | | Zymomonas mobilis pdc | ADK13058.1 |
| Primary aldehyde → Primary alcohol | A primary aldehyde + NAD(P)H → A primary alcohol | 1.1.1.- | Alcohol dehydrogenase | E. coli betA | NP_414845.1 |
| | | | | E. coli dkgA | NP_417485.4 |
| | | | | E. coli eutG | NP_416948.4 |
| | | | | E. coli fucO | NP_417279.2 |
| | | | | E. coli ucpA | NP_416921.4 |
| | | | | E. coli yahK | NP_414859.1 |
| | | | | E. coli ybbO | NP_415026.1 |
| | | | | E. coli ybdH | NP_415132.1 |
| | | | | E. coli yiaY | YP_026233.1 |
| | | | | E. coli yjgB | NP_418690.4 |
| | | | | Saccharomyces cerevisiae ADH6 | Q04894.1 |
| | | | | Clostridium kluyveri 4hbD | EDK35022.1 |
| | | | | Acinetobacter sp. SE19 chnD | AAG10028.1 |
| 2-hydroxyacyl-CoA → primary aldehyde + formyl-CoA | A 2-hydroxyacyl-CoA → A formyl-CoA + A primary aldehyde | 4.1.-.- | 2-hydroxyacyl-CoA lyase | Homo sapiens hac1 | Q9UJ83 |
| | | | | Rattus norvegicus hac1 | Q8CHM7 |
| | | | | Dictyostelium discoideum hac1 | Q54DA9 |
| | | | | Mus musculus hac1 | Q9QXE0 |

All strains used in this study are listed in Table 6. Gene deletions were performed using P1 phage transduction with single-gene knockout mutants from the National BioResource Project (NIG, Japan) as the specific deletion donor. The λDE3 prophage, carrying the T7 RNA polymerase gene and lacIq, was integrated into the chromosome through λDE3 lysogenization kit (Novagen, Darmstadt, Germany). All strains were stored in 32.5% glycerol stocks at −80° C. Plates were prepared using LB medium containing 1.5% agar, and appropriate antibiotics were included at the following concentrations: ampicillin (100 μg/mL), spectinomycin (50 μg/mL), kanamycin (50 μg/mL), and chloramphenicol (34 μg/mL).

All plasmids used in this study and oligonucleotides used in their construction are listed in Tables 6 and 7. Plasmid based gene overexpression was achieved by cloning the desired gene(s) into either pETDuet-1 or pCDFDuet-1 (Novagen, Darmstadt, Germany) digested with appropriate restriction enzymes using In-Fusion PCR cloning technology (Clontech Laboratories, Inc., Mountain View, Calif.). Cloning inserts were created via PCR of ORFs of interest from their respective genomic or codon-optimized DNA with Phusion polymerase (Thermo Scientific, Waltham, Mass.). E. coli genes were obtained from genomic DNA, while heterologous genes were synthesized by GenScript (Piscataway, N.J.) or GeneArt (Life Technologies, Carlsbad, Calif.) with codon optimization except for bktB, phaB1, and pct, which were amplified from genomic DNA or cDNA of their source organisms. The resulting In-Fusion products were used to transform E. coli Stellar cells (Clontech Laboratories, Inc., Mountain View, Calif.) and PCR identified clones were confirmed by DNA sequencing

TABLE 6

Strains and plasmids used in this study.

| Strain/plasmid | Genotype |
| --- | --- |
| *E. coli* Strains | |
| MG1655 | F-λ-ilvG-rfb-50 rph-1 |
| JC01 | MG1655 ΔldhA::FRT ΔpoxB::FRT Δpta::FRT ΔadhE::FRT ΔfrdA::FRT |
| JC01(DE3) | JC01 with DE3, a λ prophage carrying the T7 RNA polymerase gene and lacI$^q$ |
| JST06 | JC01 ΔyciA:FRT ΔybgC::FRT Δydil::FRT ΔtesA::FRT ΔfadM::FRT ΔtesB::FRT |
| JST06(DE3) | JST06 with DE3, a λ prophage carrying the T7 RNA polymerase gene and lacI$^q$ |
| MG1655(DE3) | MG1655 with DE3, a λ prophage carrying the T7 RNA polymerase gene and lacI$^q$ |
| MG1655(DE3) ΔglcD | MG1655(DE3) ΔglcD::FRT |
| BL21(DE3) | F- ompT gal dcm lon hsdS$_B$(r$_B^-$m$_B^-$) λ(DE3 [lacI lacUV5-T7 gene 1 ind1 sam7 nin5]) [malB$^+$]$_{K-12}$(λ$^S$) |
| *S. cerevisiae* strains | |
| INVSc1 | MATa his3D1 leu2 trp1-289 ura3-52 MAT his3D1 leu2 trp1-289 ura3-52 |
| Plasmids | |
| pETDuet | ColE1(pBR322) ori, lacI, T7lac, |
| pETDuet-P1-fadB2x-fadB1x | ColE1 ori; Amp$^R$; P$_{T7lac-1}$: fadB2x-fadB1x |
| pETDuet-P1-fadB2x-fadB1x-P2-ydil | ColE1 ori; Amp$^R$; P$_{T7lac-1}$: fadB2x-fadB1x P$_{T7lac-2}$: ydil |
| pETDuet-P1- bktB-phaB1 | ColE1 ori; Amp$^R$; P$_{T7lac-1}$: bktB-phaB1 |
| pETDuet-P1- bktB-phaB1-P2-phaJ | ColE1 ori; Amp$^R$; P$_{T7lac-1}$: bktB-phaB1 P$_{T7lac-2}$: phaJ |
| pCDFDuet-1 | CloDF13 ori, lacI, T7lac, Strep$^R$ |
| pCDFDuet-P1-pct-fadAx | CloDF13 ori; Strep$^R$; P$_{T7lac-1}$: pct-fadAx |
| pCDFDuet-P1-pct-fadAx-P2-fabI | CloDF13 ori; Strep$^R$; P$_{T7lac-1}$: pct-fadAx P$_{T7lac-2}$: fabI |
| pCDFDuet-P1-pct-P2-tdTer | CloDF13 ori; Strep$^R$; P$_{T7lac-1}$: pct P$_{T7lac-2}$: tdTer |
| pCDFDuet-1-P1-ntH6-HACL1 | CloDF13 ori; Strep$^R$; P$_{T7lac-1}$: ntHis6-HACL1 |
| pYE260-HACL1 | ColE1 ori; Amp$^R$; P$_{GAL1}$: ntHis6-HACL1 |

TABLE 7

Oligonucleotides used in this study for plasmid constructions

| Name | Sequence |
| --- | --- |
| pct-f1 | 5'-AGGAGATATACCATGAGAAAAGTAGAAATCATTAC-3' |
| pct-r1 | 5'-CGCCGAGCTCGAATTCTTATTTTTTCAGTCCCATGGGAC-3' |
| fabI-f1 | 5'-AAGGAGATATACATATGGGTTTTCTTTCCGGTAAG-3' |
| fabI-r1 | 5'-TTGAGATCTGCCATATGTTATTTCAGTTCGAGTTCGTTC-3' |
| fadAx-f1 | 5'-GAAAAATAAGAATTTAAGGAGGAATAAACCATGACCCTGGCAAATGATCC-3' |
| fadAx-r1 | 5'-CGCCGAGCTCGAATTCTTAATACAGACATTCAACTGCC-3' |
| fadB2x-f1 | 5'-AGGAGATATACCATGCATATCGCCAACAAACAC-3' |
| fadB2x-r1 | 5'-CGCCGAGCTCGAATTCTTATTTTGCTGCCATGCGCAG-3' |
| fadB1x-f1 | 5'-AGCAAAATAAGAATTTAAGGAGGAATAAACCATGGCCTTTGAAACCATTCTG-3' |
| fadB1x-r1 | 5'-CGCCGAGCTCGAATTCTTAGCGATCTTTAAACTGTGC-3' |
| ydil-f1 | 5'-AAGGAGATATACATATGATATGGAAACGGAAAATCAC-3' |
| ydil-r1 | 5'-TTGAGATCTGCCATATGTCACAAAATGGCGGTCGTC-3' |
| bktB-f1 | 5'-AGGAGATATACCATGATGACGCGTGAAGTGGTAGT-3' |
| bktB-r1 | 5'-CGCCGAGCTCGAATTCTCAGATACGCTCGAAGATGG-3' |
| phaB1-f1 | 5'-GCGTATCTGAGAATTAGGAGGCTCTCTATGACTCAGCGCATTGCGTA |

TABLE 7-continued

Oligonucleotides used in this study for plasmid constructions

| Name | Sequence |
|---|---|
| phaB1-r1 | 5'-CGCCGAGCTCGAATTCTCAGCCCATGTGCAGGCC-3' |
| phaJ-f1 | 5'-AAGGAGATATACATATGTCGGCACAAAGCCTG-3' |
| phaJ-r1 | 5'-TTGAGATCTGCCATATGTTACGGCAGTTTCACCACC-3' |
| HACL1-f1 | 5'-GCCAGGATCCGAATTctATGCCGGACAGCAACTTC-3' |
| HACL1-r1 | 5'-CGCCGAGCTCGAATTcTTACATATTGCTACGGGTCAGC-3' |

Fermentation medium and conditions: The minimal medium designed by Neidhardt et al. with 125 mM MOPS and $Na_2HPO_4$ in place of $K_2HPO_4$ (1.48 mM for fermentations in flasks; 2.8 mM for fermentations in bioreactors), supplemented with 20 g/L glycerol, 10 g/L tryptone, 5 g/L yeast extract, 100 µM $FeSO_4$, 5 mM calcium pantothenate, 5 mM $(NH_4)_2SO_4$, and 30 mM $NH_4Cl$ was used for all fermentations unless otherwise stated. Neutralized 20 mM glycolic acid or propionic acid was supplemented as needed. Antibiotics (50 µg/mL carbenicillin and 50 µg/mL spectinomycin) were included when appropriate. All chemicals were obtained from Fisher Scientific Co. (Pittsburgh, Pa.) and Sigma-Aldrich Co. (St. Louis, Mo.).

Unless otherwise stated, fermentations were performed in 25 mL Pyrex Erlenmeyer flasks (narrow mouth/heavy duty rim, Corning Inc., Corning, N.Y.) filled with 20 mL fermentation medium and sealed with foam plugs filling the necks. A single colony of the desired strain was cultivated overnight (14-16 h) in LB medium with appropriate antibiotics and used as the inoculum (1%). After inoculation, flasks were incubated in a NBS 124 Benchtop Incubator Shaker (New Brunswick Scientific Co., Inc., Edison, N.J.) at 200 rpm and 37° C., except fermentations supplemented with phenylacetic acid or isobutyric acid in which the temperature was 30° C. When optical density (550 nm, OD550) reached ~0.3-0.5, 5 µM isopropyl β-d-1-thiogalactopyranoside (IPTG) was added for plasmid based gene expression in all cases except the following: 1 µM IPTG was used for adipic acid production from glycerol without succinic acid supplementation and 10 µM IPTG was used during production of ω-phenylalkanoic acids. For induction of controlled chromosomal expression constructs, 0.1 mM cumate and 15 ng/mL anhydrotetracycline were also added when appropriate. Flasks were then incubated under the same conditions for 48 h post-induction unless otherwise stated.

Additional fermentations were conducted in a SixFors multi-fermentation system (Infors HT, Bottmingen, Switzerland) with an air flow rate of 2 N L/hr, independent control of temperature (37° C.), pH (controlled at 7.0 with NaOH and $H_2SO_4$), and stirrer speed (720 rpm). Tiglic acid fermentations used the previously described fermentation media with 30 g/L glycerol, the inclusion of 5 µM sodium selenite, and 5 µM IPTG. Propionic acid (20 mM) was added at 0, 24, and 48 h. Pre-cultures were grown in 25 mL flasks as described above, incubated for 4 h post-induction, and used for inoculation as described above.

Fermentations with glycolyl-CoA as a primer were conducted in 250 mL Erlenmeyer Flasks filled with 50 mL LB media supplemented with 10 g/L glucose and appropriate antibiotics. The cultivation of inoculum was same as above but 2% inoculation was used. After inoculation, cells were cultivated at 30° C. and 250 rpm in a NBS 124 Benchtop Incubator Shaker until an optical density of ~0.8 was reached, at which point IPTG (0.1 mM) and neutralized glycolic acid (40 mM) were added. Flasks were then incubated under the same conditions for 96 h post induction.

GC sample preparation: Sample preparation was conducted as follows: 2 mL culture supernatant samples were transferred to 5 mL glass vials (Fisher Scientific Co., Fair Lawn, N.J., USA) and 80 µL of 50% $H_2SO_4$ and 340 µL of 30% NaCl solution were added for pH and ionic strength adjustment, respectively. Tridecanoic acid (final concentration 50 mg/L) was added as internal standard and 2 mL of hexane-MTBE (1:1) added for extraction. The bottles were sealed with Teflonlined septa (Fisher Scientific Co., Fair Lawn, N.J., USA), secured with caps, and rotated at 60 rpm for 120 min. The samples were then centrifuged for 2 min at 2,375×g to separate the aqueous and organic layers. 1 mL of the dry organic layer was transferred into a 2 mL borosilicate glass vial, dried under $N_2$, and re-suspended in 100 µL of pyridine. After vortexing, 100 µL of BSTFA (N,O-bis(trimethylsilyl)trifluoroacetamide) was added, the samples were heated at 70° C. for 30 min, dried under $N_2$ and re-suspended in 1 mL hexane for analysis.

GC-MS metabolite identification: Except identifications of 2,3-dihydroxybutyric acid, metabolite identification was conducted via GC-MS in an Agilent 7890A GC system (Agilent Technologies, Santa Clara, Calif.), equipped with a 5975C inert XL mass selective detector (Agilent) and Rxi-5Sil column (0.25 mm internal diameter, 0.10 µm film thickness, 30 m length; Restek, Bellefonte, Pa.). The sample injection amount was 2 µL with 40:1 split ratio. The injector and detector were maintained at 280° C. The column temperature was held initially at 35° C. for 1 min and increased to 200° C. at the rate of 6° C./min, then to 270° C. at the rate of 30° C./min. That final temperature was maintained for 1 min before cooling back to initial temperature. The carrier gas was helium (2.6 mL/min, Matheson Tri-Gas, Longmont, Colo.).

Identification of 2,3-dihydroxybutyric acid was conducted by the Baylor College of Medicine Analyte Center (bcm.edu/research/centers/analyte, Houston, Tex.). An Agilent 6890 GC system (Agilent Technologies, Santa Clara, Calif.), equipped with a 5973 mass selective detector (Agilent Technologies) and HP-5 ms column (Agilent Technologies) was used. Sample extraction was conducted using Agilent Chem Elut liquid extraction columns (Agilent Technologies) according to manufacturer protocols.

HPLC metabolite quantification: The concentration of products were determined via ion-exclusion HPLC using a Shimadzu Prominence SIL 20 system (Shimadzu Scientific Instruments, Inc., Columbia, Md.) equipped with an HPX-87H organic acid column (Bio-Rad, Hercules, Calif.) with operating conditions to optimize peak separation (0.3 ml/min flow rate, 30 mM $H_2SO_4$ mobile phase, column temperature 42° C.).

In vitro enzyme assay: Purified HACL1 was tested for its native catabolic activity by assessing its ability to cleave 2-hydroxyhexadecanoyl-CoA to pentadecanal and formyl-CoA. Enzyme assays were performed in 50 mM tris-HCl pH 7.5, 0.8 mM $MgCl_2$, 0.02 mM TPP, 6.6 μM BSA, and 0.3 mM 2-hydroxyhexadecanoyl-CoA. The assay mixtures were incubated for one hour at 37° C., after which the presence of pentadecanal was assessed by extraction with hexane and analysis by GC-FID.

2-hydroxyhexadecanoyl-CoA was prepared by the n-hydroxysuccinimide method. In summary, the n-hydroxysuccinimide ester of 2-hydroxyhexadecanoic acid is prepared by reacting n-hydroxysuccinimide with the acid in the presence of dicyclohexylcarbodiimide. The product was filtered and purified by recrystallization from methanol to give pure n-hydroxysuccinimide ester of 2-hydroxyhexadecanoic acid. The ester was reacted with CoA-SH in presence of thioglycolic acid to give 2-hydroxyhexadecanoyl-CoA. The 2-hydroxyhexadecanoyl-CoA was purified precipitation using perchloric acid, filtration, and washing the filtrate with perchloric acid, diethyl ether, and acetone.

For specific activity assays (reported in μmol substrate/mg protein/min) these supernatant fractions were utilized and protein concentration was established using the Bradford Reagent (Thermo Sci.) using BSA as the protein standard.

Enzyme purification: A plasmid containing the codon optimized gene encoding human HIS-tagged HACL1 was constructed as described. The resulting construct was transformed into *S. cerevisiae* InvSC1 (Life Tech.). The resulting strain was cultured in 50 mL of SC-URA media containing 2% glucose at 30° C. for 24 hours. The cells were pelleted and the required amount of cells were used to inoculate a 250 mL culture volume of SC-URA media containing 0.2% galactose, 1 mM $MgCl_2$, and 0.1 mM thiamine to 0.4 OD600. After 20 hours incubation with shaking at 30° C., the cells were pelleted and saved.

When needed, the cell pellets were resuspended to an OD600 of approximately 100 in a buffer containing 50 mM potassium phosphate pH 7.4, 0.1 mM thiamine pyrophosphate, 1 mM $MgCl_2$, 0.5 mM AEBSF, 10 mM imidazole, and 250 units of Benzonase nuclease. To the cell suspension, approximately equal volumes of 425-600 μm glass beads were added. Cells were broken in four cycles of 30 seconds of vortexing at 3000 rpm followed by 30 seconds on ice. The glass beads and cell debris were pelleted by centrifugation and supernatant containing the cell extract was collected. The HIS-tagged HACL1 was purified from the cell extract using Talon Metal Affinity Resin as described above, with the only modification being the resin bed volume and all subsequent washes were halved. The eluate was collected in two 500 μL fractions.

Expression and purification of the desired protein can be confirmed by running cell pellet sample and eluate on SDS-PAGE.

Figure 5:
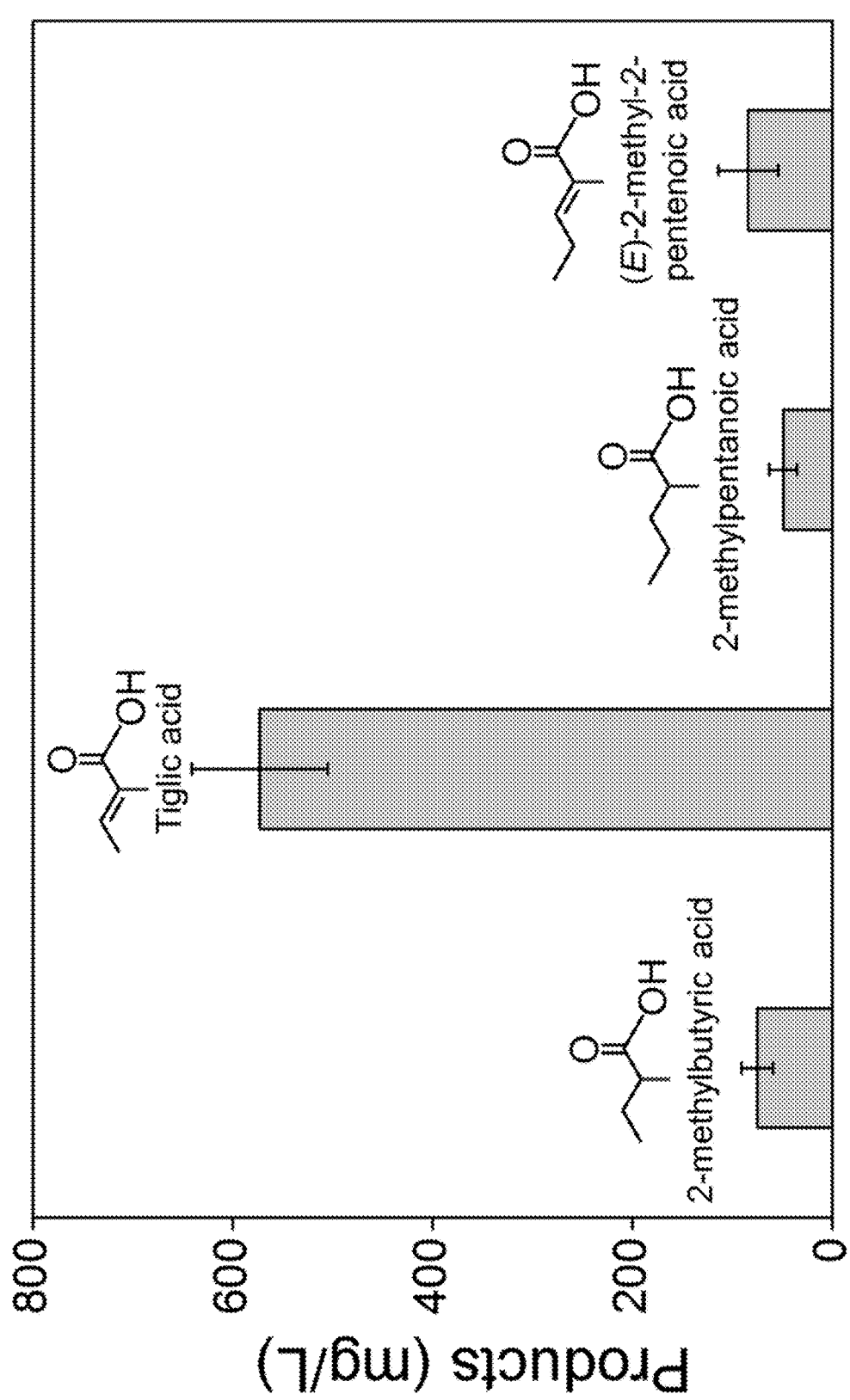
FIG. 5: Titers of alpha-methylated products synthesized through the utilization of propionyl-CoA as the extender unit with either acetyl-CoA or propionyl-CoA priming. These products were produced from the E. coli strain overexpressing enzymes catalyzing Steps 1-5 depicted in FIG. 3-4. JC01(DE3), an E. coli strain deficient of mixed-acid fermentations, served as the host strain. The engineered strains were grown for 48 hours under 37° C. in 20 mL LB-like MOPS media supplemented with 20 g/L glycerol and 20 mM propionic acid.
Figure 6:
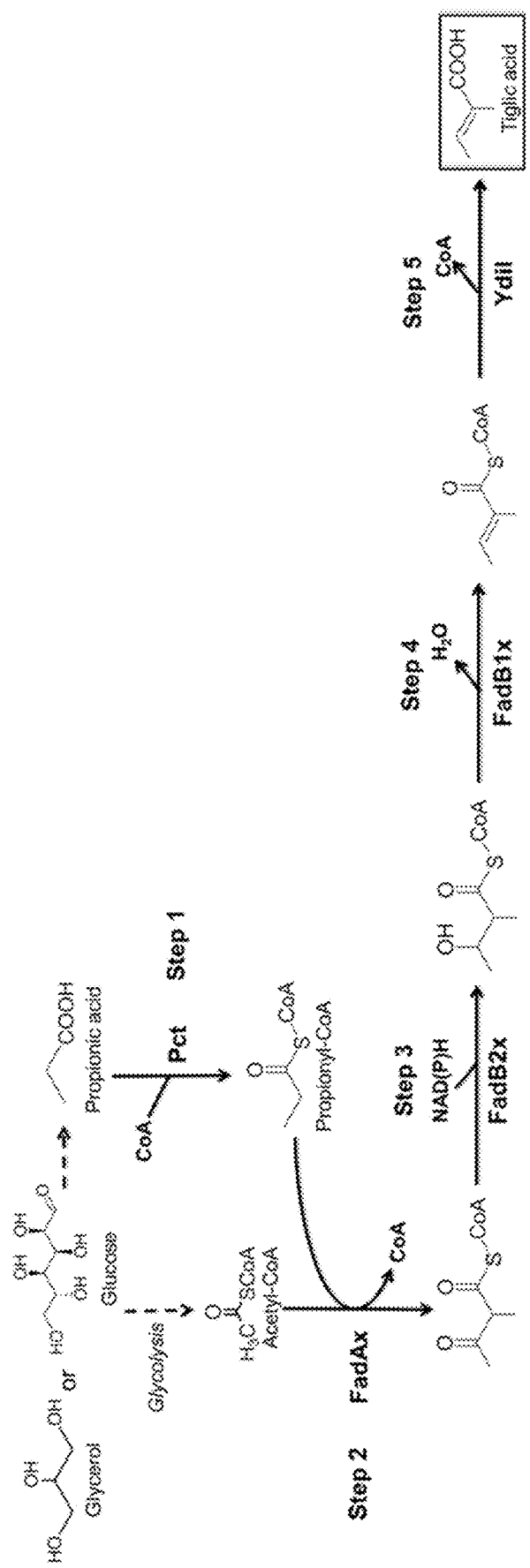
FIG. 6: Pathway for the improved production of tiglic acid through the proposed platform with acetyl-CoA as the primer and propionyl-CoA as the extender unit. Propionyl-CoA is activated by Pct from propionic acid (Step 1). Thiolase FadAx condenses acetyl-CoA and propionyl-CoA to 2-methyl acetoacetyl-CoA (Step 2). Dehydrogenase FadB2x converts 2-methyl acetoacetyl-CoA to 2-methyl-3-hydroxybutyryl-CoA (Step 3). Dehydratase FadB1x converts 2-methyl-3-hydroxybutyryl-CoA to tiglyl-CoA (Step 4). Finally, thioesterase YdiI can remove the CoA from tiglyl-CoA to generate the product tiglic acid (Step 5).

We demonstrated several cases of the iterative system can synthesize alpha-functionalized small molecules through the use of alpha-functionalized forms of acetyl-CoA as the extender unit. One case used of propionyl-CoA as the extender unit. To implement this, *P. putida* FadAx (thiolase), FadB2x (HACD), FadB1x (ECH), and *E. coli* FabI (ECR) were used with Pct for activation of exogenous propionic acid. Expression in JC01(DE3) resulted in the production of 2-methylbutyric acid (75 mg/L) and tiglic acid (573 mg/L) (FIG. 5), representing products of acid-forming endogenous termination enzymes at the acyl-CoA and enoyl-CoA pathway nodes.

Figure 11:
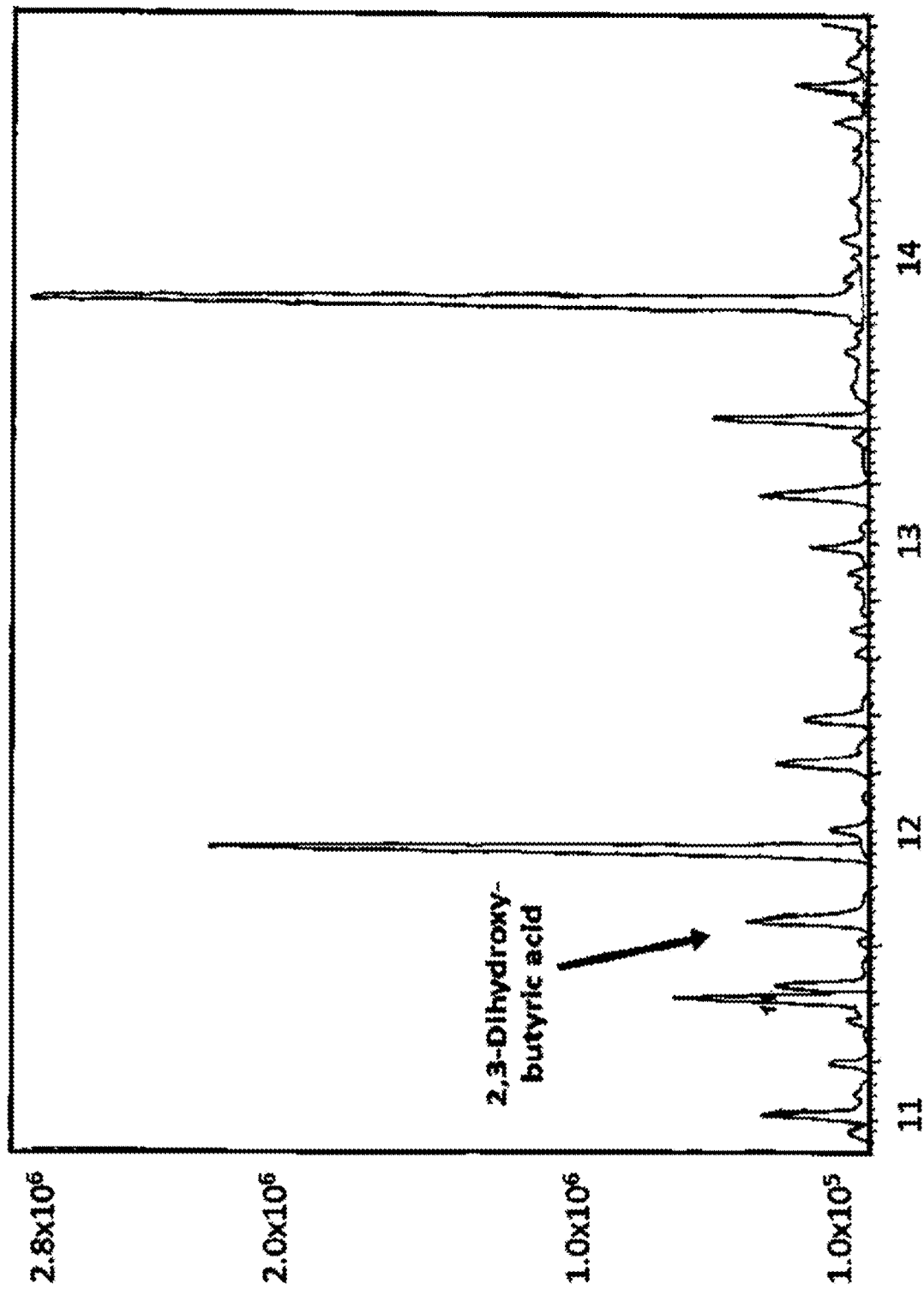
FIG. 11: Peak of product 2,3-dihydroxy-butyric acid in the GC-MS chromatogram of the fermentation sample from MG1655(DE3) ΔglcD (pET-P1-bktB-phaB-P2-phaJ) (pCDF-P1-pct-P2-tdTER). The strain was grown in 50 mL LB media supplemented with 10 g/L glucose and 40 mM glycolate for 96 hours under 30° C. in 250 mL flask.
Figure 12:
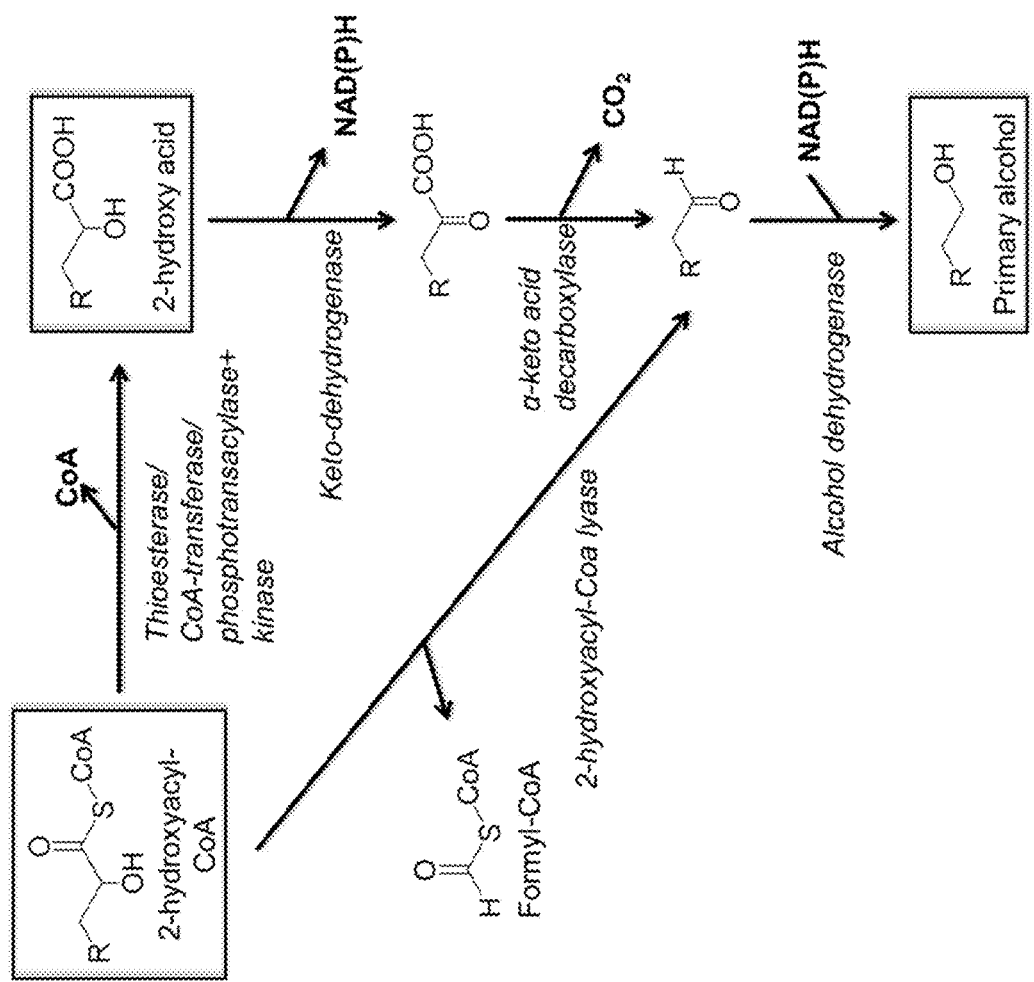
FIG. 12: Derivatization pathway of product 2-hydroxy acid and intermediate 2-hydroxyacyl-CoA of the proposed platform utilizing glycolyl-CoA as the extender unit depicted in FIG. 3, to a primary alcohol product. 2-hydroxyacyl-CoA can be degraded to primary aldehyde and formyl-CoA by 2-hydroxyacyl-CoA lyase. 2-hydroxy acid can be converted to α-keto acid by keto-dehydrogenase and α-keto acid can be decarboxylated to primary aldehyde by α-keto acid to primary aldehyde. Primary aldehyde is finally reduced to primary alcohol by alcohol dehydrogenase.
Figure 13:
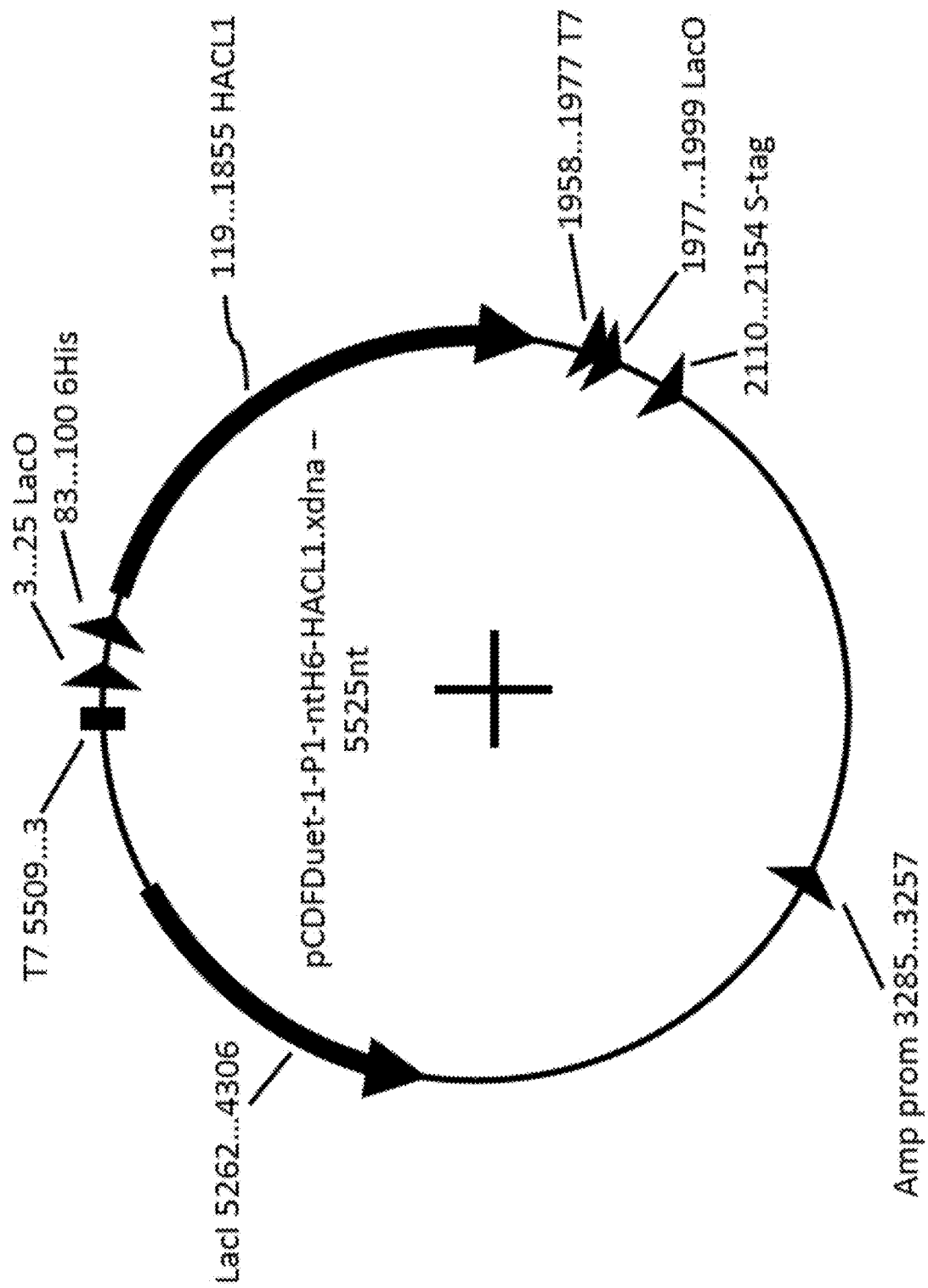
FIG. 13: Vector map of pCDFDuet-1-P1-ntH6-HACL1 for overexpression and purification of codon-optimized 2-hydroxyacyl-CoA lyase HACL1 from *Homo sapiens* in E. coli.

Interestingly, 2-methylpentanoic acid (49 mg/L) and (E)-2-methyl-2-pentenoic acid (84 mg/L) were also synthesized, as the result of propionyl-CoA serving as both the primer and the extender unit. Products resulting from non-functionalized extender units (acetyl-CoA) with acetyl-CoA or propionyl-CoA priming were also observed, demonstrating the nonspecific activity of the thiolase (and subsequent β-reduction enzymes). This represents a potential area for further improvement through the selection and engineering of a thiolase with maximal specificity for the desired condensation. Additional alpha-functionalization was demonstrated with glycolyl-CoA (i.e. α-hydroxylated acetyl-CoA) as the extender unit, which with acetyl-CoA priming supported the synthesis of 2,3-dihydroxybutyric acid (FIG. 11).

Figure 7:
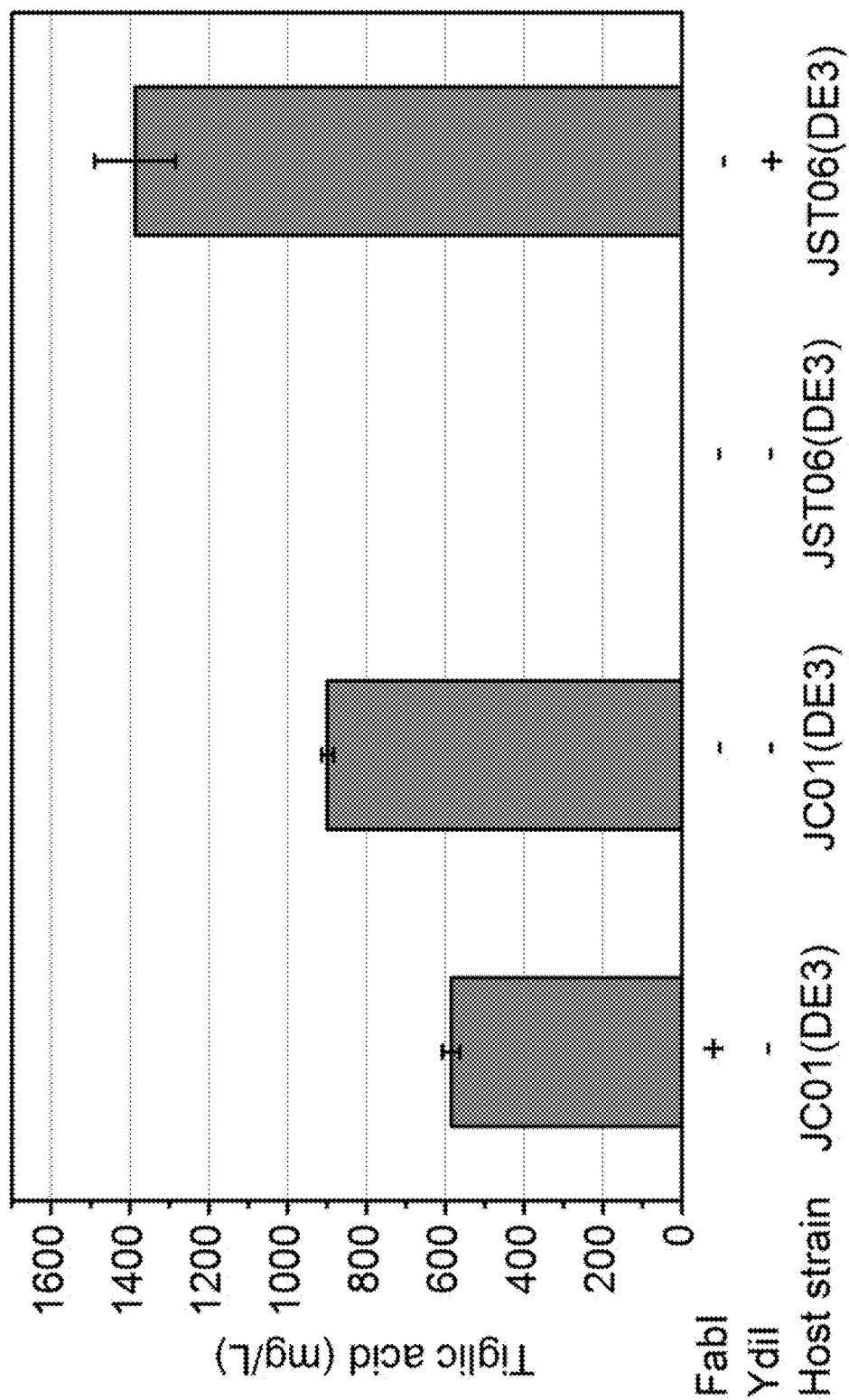
FIG. 7: Results of improvement of tiglic acid production by removal of overexpression of FabI (ECR), addition of overexpression of YdiI (a thioesterase) and usage of JST06 (DE3) as the host strain. JST06(DE3) is an E. coli strain deficient of mixed-acid fermentations, thioesterases. The engineered strains were grown for 48 h at 37° C. in 20 mL LB-like MOPS media supplemented with 20 g/L glycerol and 20 mM propionic acid.
Figure 8:
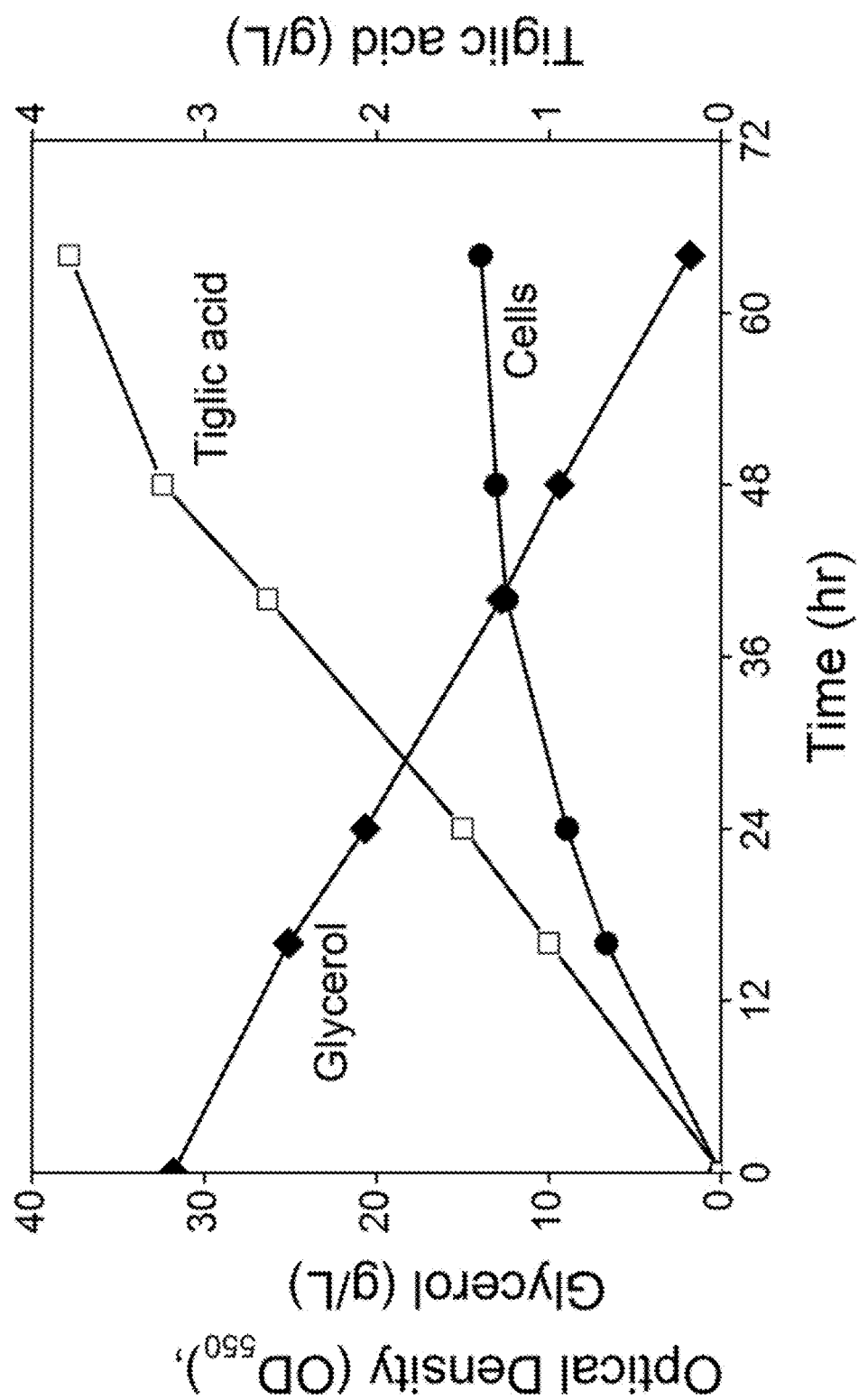
FIG. 8: Time course for tiglic acid production from JST06(DE3) strain overexpressing Pct, FadAx, FadB2x, FadB1x and YdiI in a fermentation conducted in a controlled bioreactor. The fermentation was performed under 37° C. in LB-like MOPS media supplemented with 30 g/L glycerol, and 20 mM propionic acid which was added at 0, 24, and 48 h.
Figure 9A:
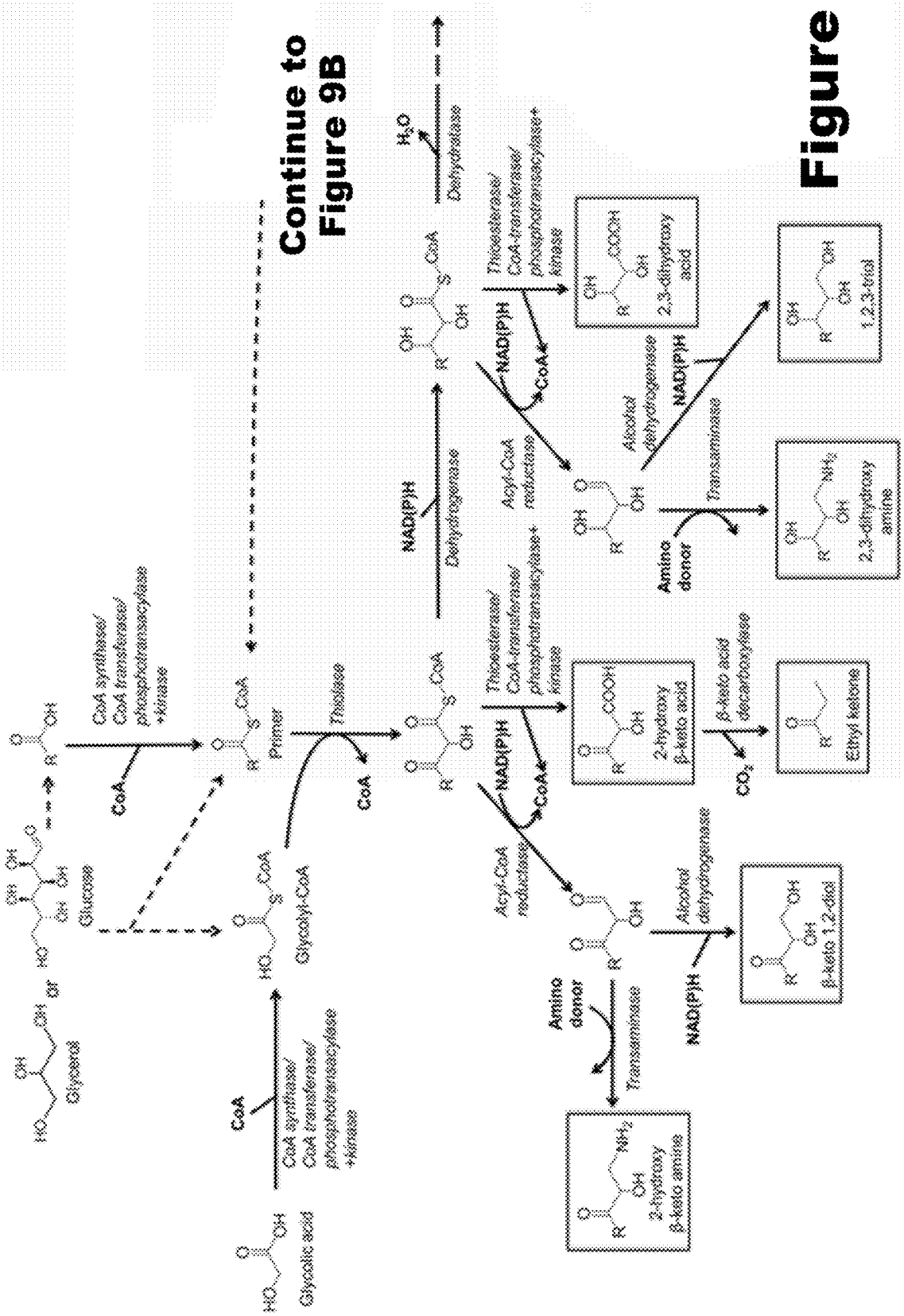
FIG. 9: Proposed platform depicted in FIG. 1 and its products utilizing glycolyl-CoA as the extender unit (R2 in FIG. 1=—OH).
Figure 9B:
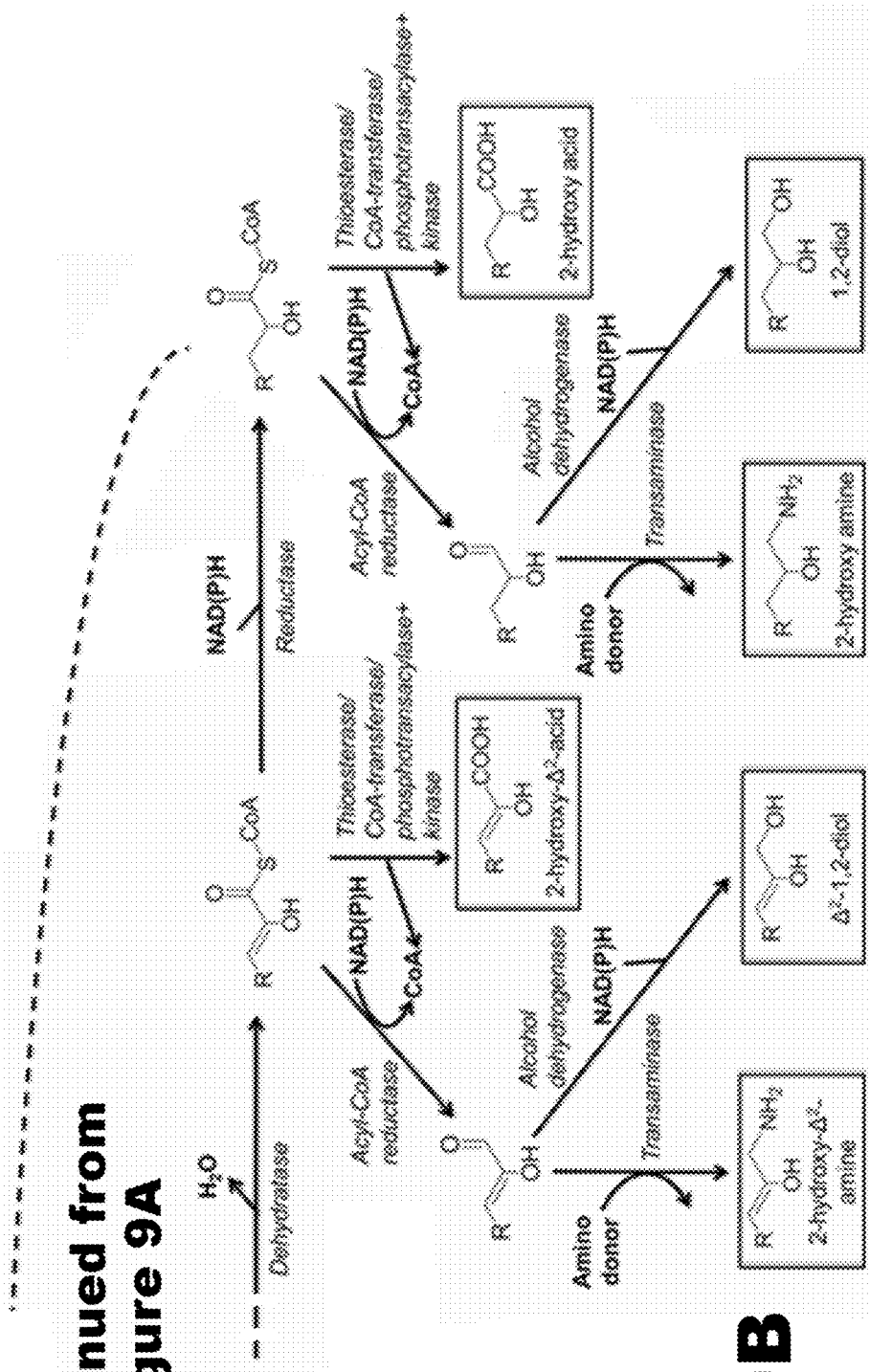
Figure 10:
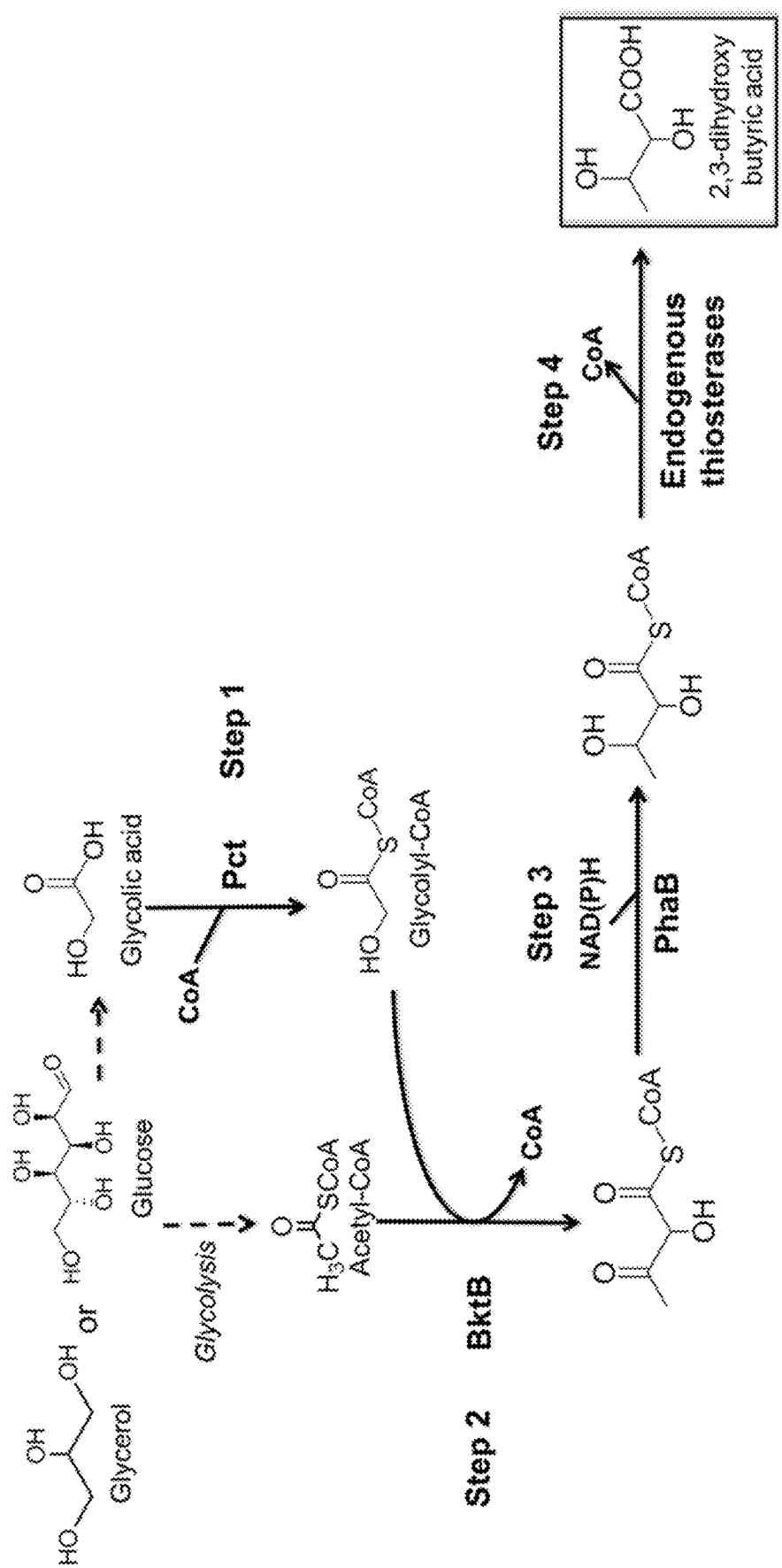
FIG. 10: Example pathway of synthesis of 2,3-dihydroxybutyric acid through the proposed platform with acetyl-CoA as the primer and propionyl-CoA as the extender unit. Glycolyl-CoA is activated by Pct from glycolic acid (Step 1). Then, condensation by thiolase BktB converts glycolyl-CoA and acetyl-CoA to 2-hydroxy acetoacetyl-CoA (Step 2). Dehydrogenase PhaB converts 2-hydroxy acetoacetyl-CoA to 2,3-dihydroxy-butyryl-CoA (Step 3). CoA removal by endogenous thioesterases convert 2,3-dihydroxy-butyryl-CoA to the product 2,3-dihydroxy-butyric acid (Step 4).

The ability of the alpha-functionalization system to support high product titers was investigated by improving tiglic acid production. Omission of ECR and manipulation of the termination pathway through deletion of native thioesterases and controlled overexpression of YdiI, a thioesterase previously shown to act effectively on α,β-unsaturated enoyl-CoAs, resulted in further improvement, from 573 mg/L to 1.39 g/L (FIG. 7). When a controlled bioreactor with a higher initial glycerol concentration was used, tiglic acid production increased to 3.79 g/L (11.6% mol/mol glycerol) (FIG. 8).

The host strains and plasmids used for production of above products are summarized in Table 8.

TABLE 8

Host strains and plasmids enabling alpha-functionalized small molecule synthesis with listed primer/extender unit combinations

| Host strain | Plasmid 1 | Plasmid 2 | Primer | Extender unit | Product |
| --- | --- | --- | --- | --- | --- |
| JC01(DE3) | pETDuet-P1-fadB2x-fadB1x | pCDFDuet-P1-pct-fadAx-P2-fabI | Acetyl-CoA | Propionyl-CoA | 2-methylbutyric acid |
| | | | | | Tiglic acid |

TABLE 8-continued

Host strains and plasmids enabling alpha-functionalized small molecule synthesis with listed primer/extender unit combinations

| Host strain | Plasmid 1 | Plasmid 2 | Primer | Extender unit | Product |
|---|---|---|---|---|---|
| | | | Propionyl-CoA | Propionyl-CoA | 2-methylpentanoic acid (E)-2-methyl-2-pentenoic acid |
| JC01(DE3) | pETDuet-P1-fadB2x-fadB1x | pCDFDuet-P1-pct-fadAx | Acetyl-CoA | Propionyl-CoA | Tiglic acid |
| JST06(DE3) | pETDuet-P1-fadB2x-fadB1x | pCDFDuet-P1-pct-fadAx | Acetyl-CoA | Propionyl-CoA | N.A. |
| JST06(DE3) | pETDuet-P1-fadB2x-fadB1x-P2-ydiI | pCDFDuet-P1-pct-fadAx | Acetyl-CoA | Propionyl-CoA | Tiglic acid |
| Acetyl-CoA | Glycolyl-CoA | 2,3-dihydroxybutyric acid | Acetyl-CoA | Glycolyl-CoA | 2,3-dihydroxybutyric acid |

Figure 14:
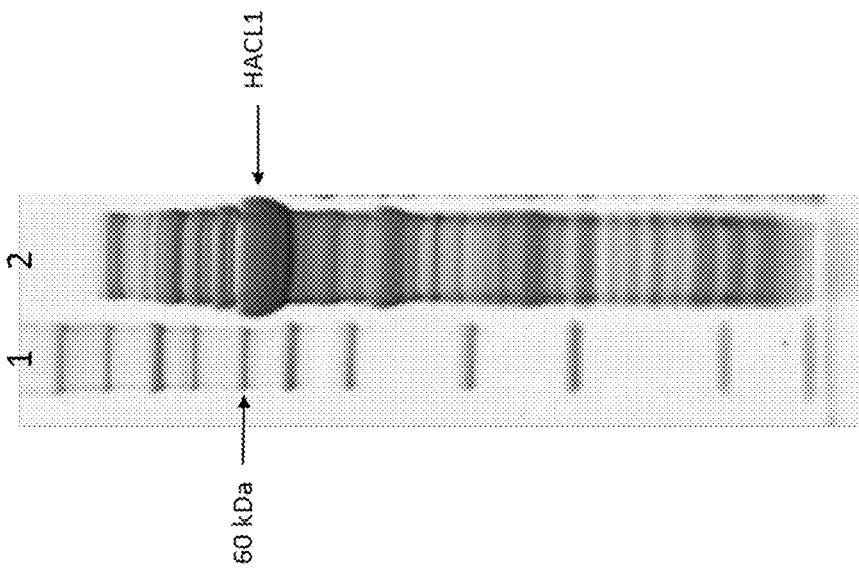
FIG. 14: SDS-PAGE analysis result of overexpression of *Homo sapiens* HACL1 in E. coli.
Figure 15:
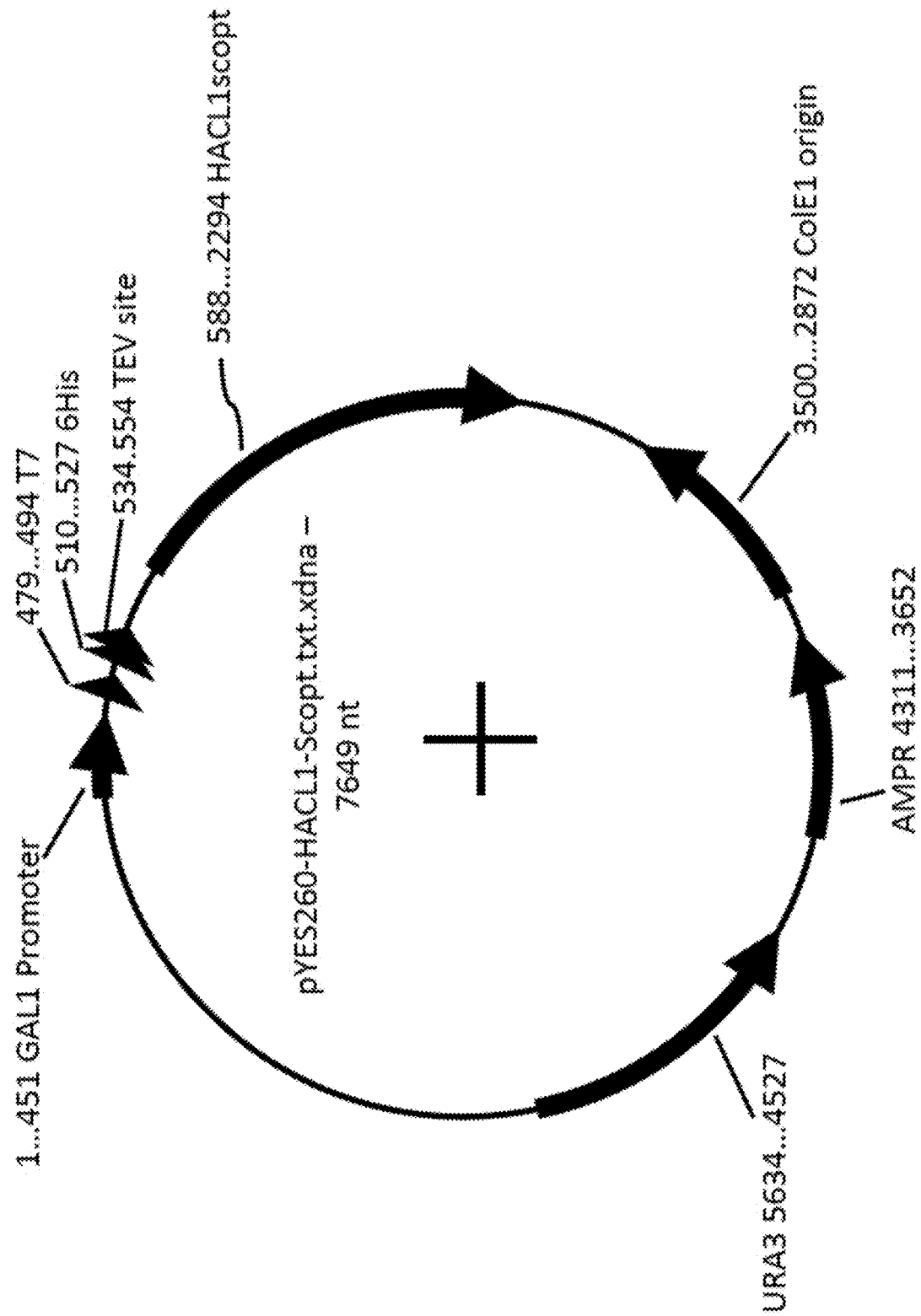
FIG. 15: Vector map of pYES260-HACL1-SCopt for overexpression and purification of codon-optimized 2-hydroxyacyl-CoA lyase HACL1 from *Homo sapiens* in *Saccharomyces cerevisiae*.
Figure 16:
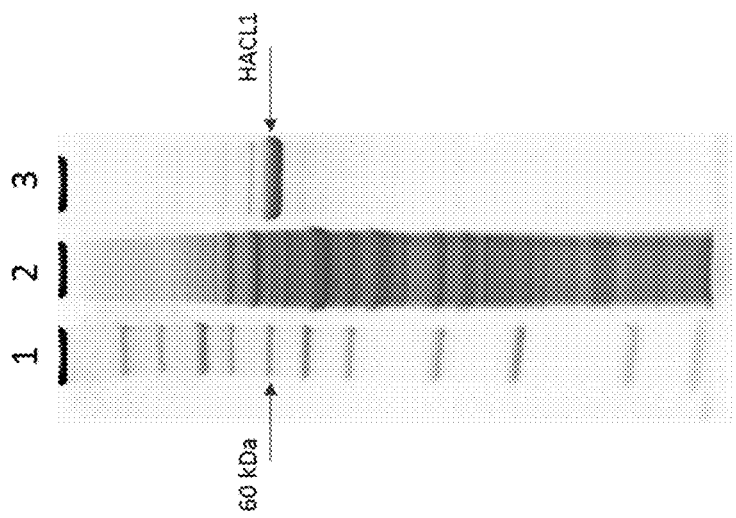
FIG. 16: SDS-PAGE analysis result of overexpression and purification of *Homo sapiens* HACL1 in S. cerevisiae.
Figure 17:
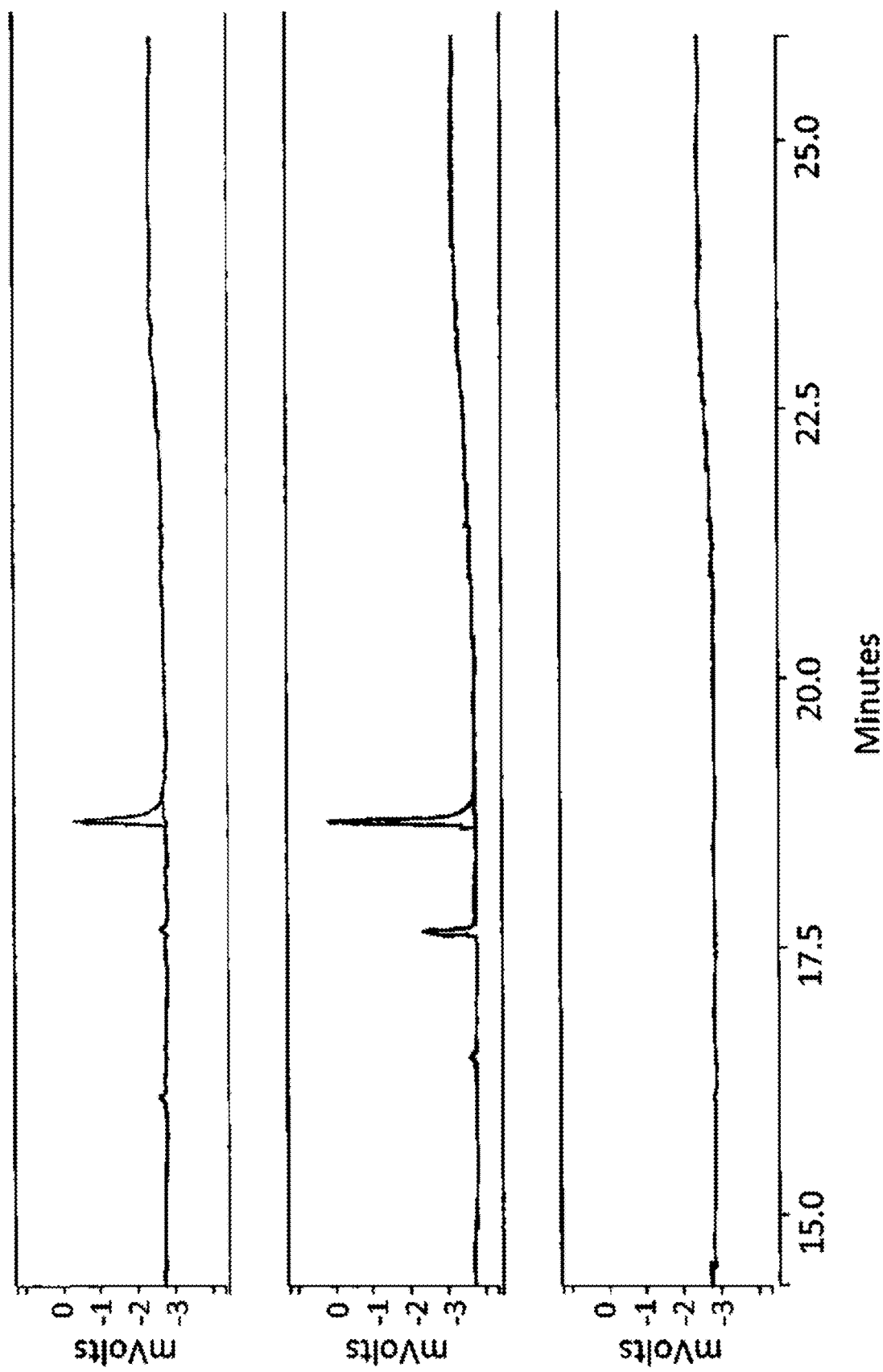
FIG. 17: GC-FID chromatograms of pentadecanal content in HACL1 degradative reaction (forward reaction) mixtures after extraction with hexane. HACL1 was expressed and purified from S. cerevisiae. Top: pentadecanal standard; Middle: HACL1 assay sampled; Bottom: no enzyme control. In samples containing HACL1, a pentadecanal peak is seen, while there is no peak in the sample in which enzyme was omitted.
Figure 18:
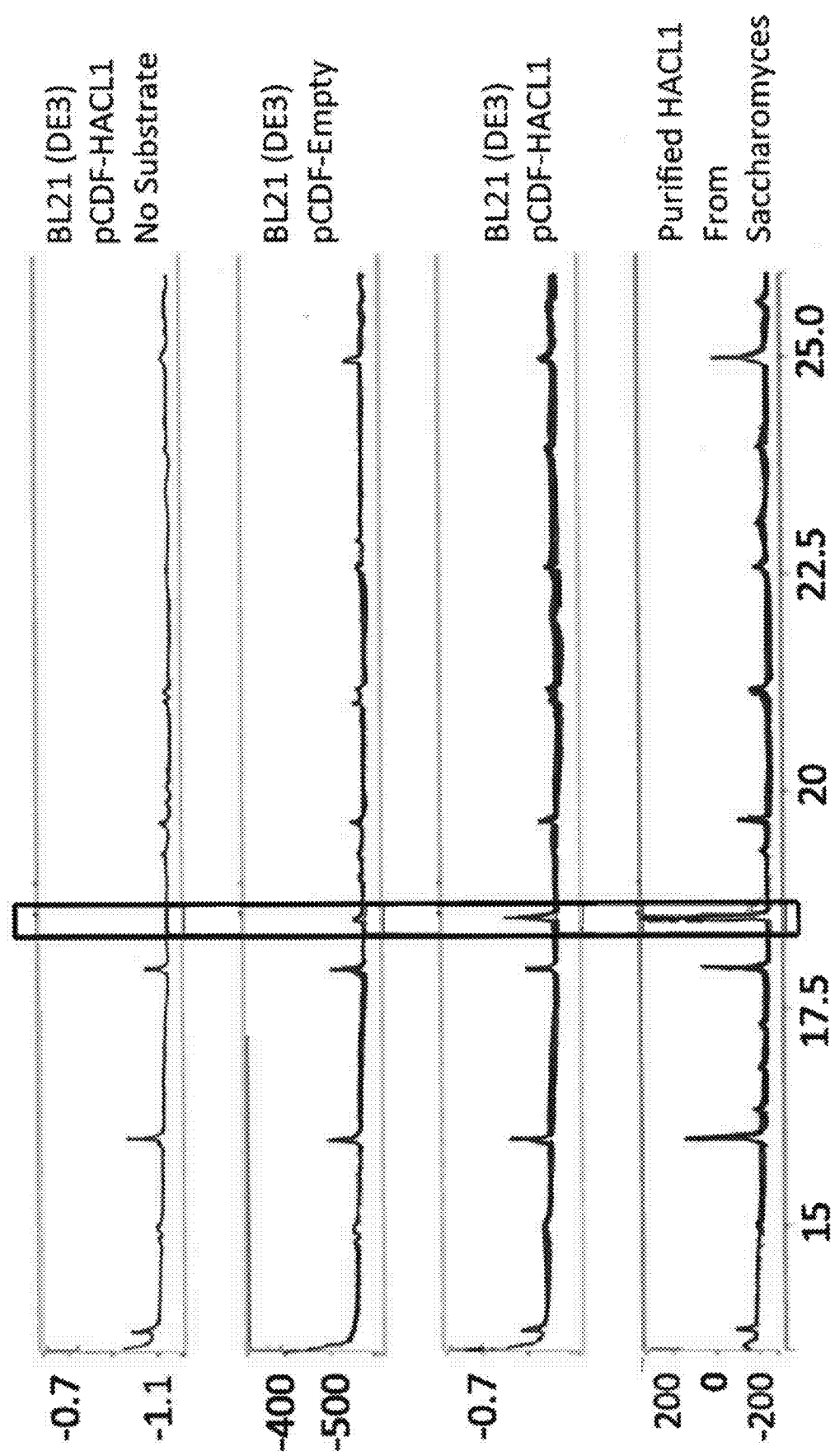
FIG. 18: GC-FID chromatograms of pentadecanal content demonstrating HACL1 activity in E. coli BL21(DE3) crude extract. The peak of pentadecanal is shown in the square.
Figure 19A:
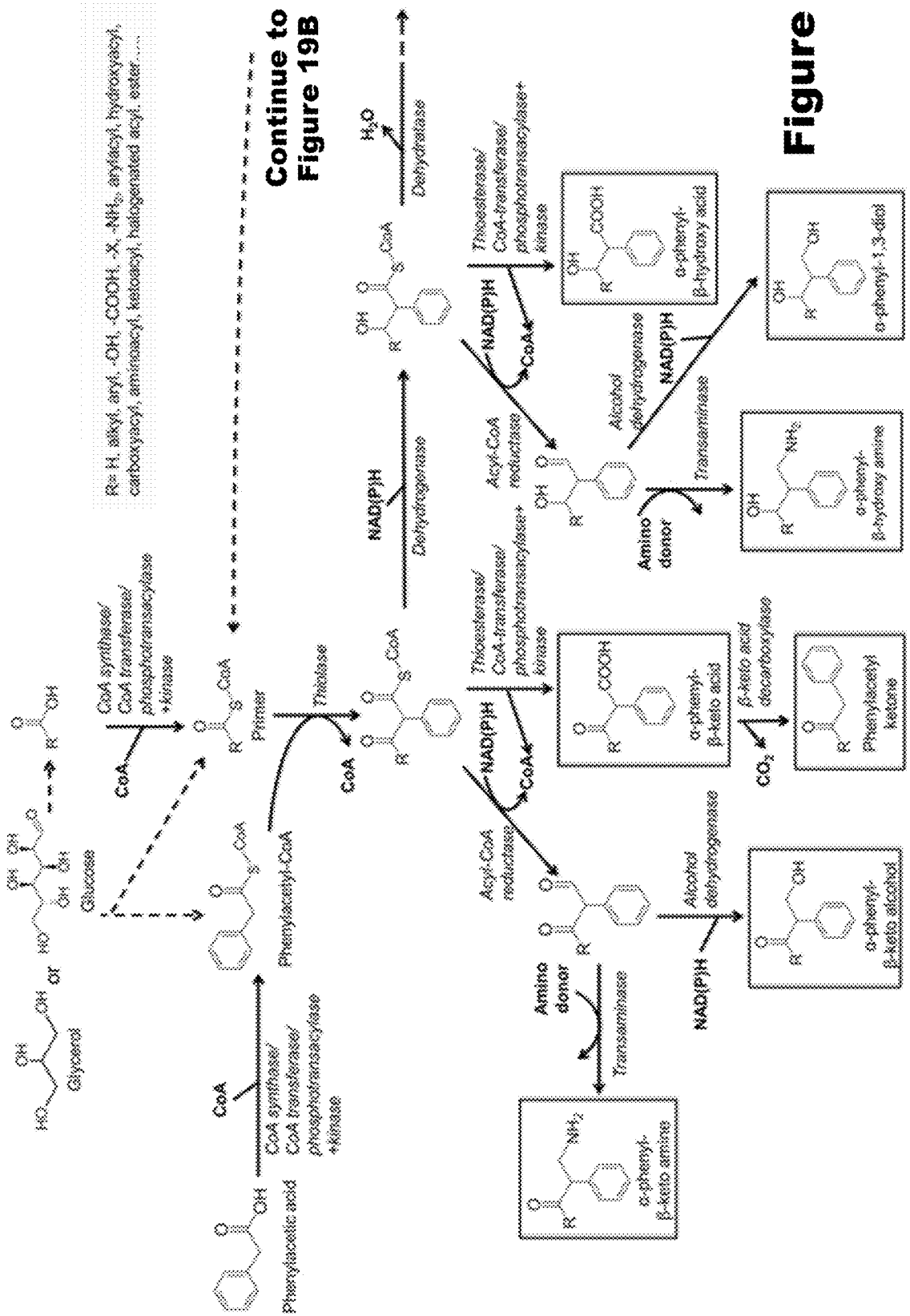
FIG. 19: Proposed platform depicted in FIG. 1 and its products utilizing phenylacetyl-CoA as the extender unit ($R_2$ in FIG. 1=-Ph).
Figure 19B:
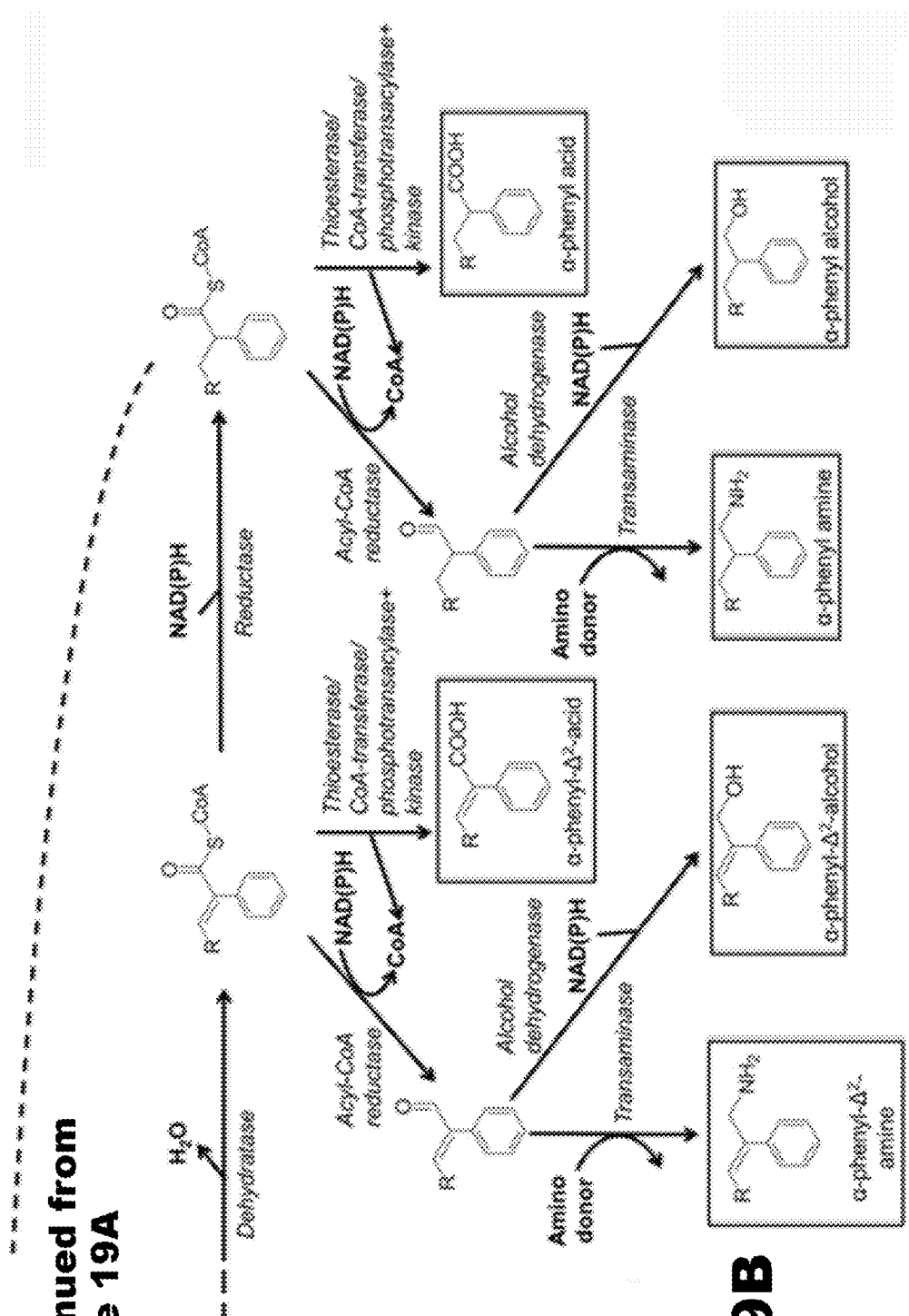

We also successfully expressed *Homo sapiens* 2-hydroxyacyl-CoA lyase HACL1 in *Saccharomyces cerevisiae* and *Escherichia coli* (FIGS. 14 and 16), and confirmed its activity of degradation of 2-hydroxyhexadecanoyl-CoA to pentadecanal (FIGS. 17-18). This provides the potential of combination of 2-hydroxyacyl-CoA lyase with proposed iterative platform using alpha-hydroxylated glycolyl-CoA as the extender unit for the synthesis of primary alcohols.

We believe that, pathway and process optimization, in line with industrial biotechnology approaches, can further improve performance for a specific target product, as the underlying carbon and energy efficiency enables the feasibility of further advancing product titer, rate, and yield. Important areas include generating and balancing pools of priming and extender units and optimization of required pathway enzymes for a given target product. The former can exploit previously developed pathways for primers and extender units, whereas the latter includes identifying and engineering enzymes that may be flux limiting due to suboptimal enzyme specificity or activity. These approaches will be continually aided by developments in protein and metabolic engineering and synthetic and systems biology.

The above experiments are repeated in *Bacillus subtilis*. The same genes can be used, especially since *Bacillus* has no significant codon bias. A protease-deficient strain like WB800N is preferably used for greater stability of heterologous protein. The *E. coli-B. subtilis* shuttle vector pMTLBS72 exhibiting full structural stability can be used to move the genes easily to a more suitable vector for *Bacillus*. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available. Since the FAS genes are ubiquitous, the invention is predicted to function in *Bacillus*.

The above experiments are repeated in yeast. The same genes can be used, but it may be preferred to accommodate codon bias. Several yeast *E. coli* shuttle vectors are available for ease of the experiments. Since the FAS genes are ubiquitous, the invention is predicted to function in yeast, especially since yeasts are already available with exogenous functional TE genes and the reverse beta oxidation pathway has also been made to run in yeast.

Each of the following is incorporated by reference herein in its entirety for all purposes:

US20130316413 Reverse beta oxidation pathway
62/140,628 BIOCONVERSION OF SHORT-CHAIN HYDROCARBONS TO FUELS AND CHEMICALS, Mar. 31, 2015
WO2015112988 TYPE II FATTY ACID SYNTHESIS ENZYMES IN REVERSE BETA-OXIDATION, Jan. 26, 2015 and 61/932,057, Jan. 27, 2014.
62/069,850 SYNTHETIC PATHWAY FOR BIOSYNTHESIS FROM 1-CARBON COMPOUNDS, Oct. 29, 2014
61/531/911, Sep. 7, 2011; 61/440,192, Feb. 7, 2011, US20140273110, WO2013036812 Functionalized carboxylic acids and alcohols by reverse fatty acid oxidation
Heath, R. J. & Rock, C. O. The Claisen condensation in biology. *Nat. Prod. Rep.* 19, 581-596 (2002).
Haapalainen, A. M., et al., The thiolase superfamily: condensing enzymes with diverse reaction specificities. *Trends in Biochemical Sciences* 31, 64-71 (2006).
Jiang, C., et al., Divergent evolution of the thiolase superfamily and chalcone synthase family. *Molecular Phylogenetics and Evolution* 49, 691-701 (2008).
Choi, K. H., et al., β-Ketoacyl-Acyl Carrier Protein Synthase III (FabH) Is a Determining Factor in Branched-Chain Fatty Acid Biosynthesis. *J. Bacteriol.* 182, 365-370 (2000).
Pfleger, B. F., et al., Metabolic engineering strategies for microbial synthesis of oleochemicals. *Metab. Eng.* 29, 1-11 (2015).
Dellomonaco, C., et al., Engineered reversal of the β-oxidation cycle for the synthesis of fuels and chemicals. *Nature* 476, 355-359 (2011).
Clomburg, J. M., et al., Synthetic Biology Approach to Engineer a Functional Reversal of the β-Oxidation Cycle. *ACS Synthetic Biology* 1, 541-554 (2012).
Vick, J. E. et al. *Escherichia coli* enoyl-acyl carrier protein reductase (FabI) supports efficient operation of a functional reversal of the β-oxidation cycle. *Appl. Environ. Microbiol.* 81, 1406-1416 (2015).
Cheong, S., Clomburg, J. M. and Gonzalez, R.* (2016). Energy- and carbon-efficient synthesis of functionalized small molecules in bacteria using non-decarboxylative Claisen condensation reactions. *Nat. Biotechnol.* 34 (5): doi:10.1038/nbt.3505.

The following claims are provided to add additional clarity to this disclosure. Future applications claiming priority to this application may or may not include the following claims, and may include claims broader, narrower, or entirely different from the following claims. Further, any detail from any claim may be combined with any other detail from another claim, even if not yet so combined.

The invention claimed is:

1. A composition comprising a genetically engineered bacteria in a media containing propionic acid or glycolic acid, said bacteria comprising a *Megasphaera elsdenii pct* gene, *Ralstonia eutropha bktB* and *phaB*1 *genes; Aeromonas caviae phaJ* gene; and *Treponema denticola TdTer* gene.

2. A composition comprising a genetically engineered bacteria in a media containing propionic acid or glycolic acid, and said bacteria comprising a *Megasphaera elsdenii pct* gene; *Pseudomonas putida fadAx, fadB*2x, *fadB*1x genes; and *E. coli YdiI* gene.

3. A composition comprising a genetically engineered bacteria in a media containing propionic acid or glycolic acid, and said bacteria comprising a *Megasphaera elsdenii pct* gene; *Pseudomonas putida fadAx, fadB*2x, *fadB*1x genes; and *E. coli FabI* gene.

* * * * *